(12) United States Patent
Bawendi et al.

(10) Patent No.: US 6,319,426 B1
(45) Date of Patent: *Nov. 20, 2001

(54) WATER-SOLUBLE FLUORESCENT SEMICONDUCTOR NANOCRYSTALS

(75) Inventors: Moungi G. Bawendi, Boston, MA (US); Frederic V. Mikulec, La Jolla, CA (US); Jin-Kyu Lee, Seoul (KR)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/397,428

(22) Filed: Sep. 17, 1999

Related U.S. Application Data

(63) Continuation-in-part of application No. 09/156,863, filed on Sep. 18, 1998, now Pat. No. 6,251,303.

(51) Int. Cl.[7] .................................................. C09K 11/00
(52) U.S. Cl. ........................... 252/301.4 R; 252/201.4 G; 252/301.6 R; 252/301.6 S; 428/690; 428/403; 428/407
(58) Field of Search ............... 252/301.4 R, 301.4 S, 252/301.6 R, 301.6 S; 428/403, 407, 690

(56) References Cited

U.S. PATENT DOCUMENTS

| | | | |
|---|---|---|---|
| 3,996,345 | 12/1976 | Ullman et al. | 424/12 |
| 4,637,988 | 1/1987 | Hinshaw et al. | 436/546 |
| 4,777,128 | 10/1988 | Lippa | 435/5 |

(List continued on next page.)

FOREIGN PATENT DOCUMENTS

| | | | |
|---|---|---|---|
| 990903 | * 4/2000 | (EP) | . |
| WO 95/29473 | 11/1995 | (WO) | . |
| WO 98/04740 | 2/1998 | (WO) | . |
| 98/19963 | 5/1998 | (WO) | . |
| WO 98/33070 | 7/1998 | (WO) | . |

(List continued on next page.)

OTHER PUBLICATIONS

Lawless et al, "Bifunctional Capping of CdS Nanoparticles and Bridging to TiO2", J. Phys. Chem., vol. 99, No. 25, pp. 10329–10335, 1995.*

Rogach et al "Synthesis and Characterization of Thiol–Stabilized CdTe Nanocrystals", Ber. Bunsenges. Phys. Chem. vol. 100, No. 11, pp. 1772–1778, 1996.*

Rajh et al, "Synthesis and Characterisctis of Surface–Modified Colloidal CdTe Quantum Dots", J. Phys. Chem., vol. 97, No. 46, pp. 11999–12003, Nov. 1993.*

Mikulec et al, "Fluorescent Semiconductor Nanocrystallites Derivatized with Biomolecules", poster presentation presented at 216th ACS national meeting and exposition, 8/23–27/98.*

Spanhel et al., "Photochemistry of Colloidal Semiconductors. Surface Modification and Stability of Strong Luminescing CdS Particles" *J. Am. Chem. Soc.*109(19):5649–5655, 1987.

(List continued on next page.)

Primary Examiner—C. Melissa Koslow
(74) Attorney, Agent, or Firm—Fish & Richardson PC

(57) ABSTRACT

A water-soluble semiconductor nanocrystal capable of light emission is provided. The nanocrystal including a semiconductor nanocrystal core having a selected band gap energy, a shell layer overcoating the core comprised of a semiconductor material having a band gap energy greater than that of the semiconductor nanocrystal, and an outer layer comprised of a molecule having at least one linking group for attachment of the molecule to the overcoating shell layer and at least one hydrophilic group optionally spaced apart from the linking group by a hydrophobic region sufficient to prevent electron charge transfer across the hydrophobic region.

31 Claims, 7 Drawing Sheets

U.S. PATENT DOCUMENTS

| | | | |
|---|---|---|---|
| 5,262,357 | 11/1993 | Alivisatos et al. | 437/233 |
| 5,293,050 | 3/1994 | Chapple-Sokol et al. | 257/17 |
| 5,304,786 | 4/1994 | Pavlidis et al. | 235/462 |
| 5,354,707 | 10/1994 | Chapple-Sokol et al. | 437/106 |
| 5,395,791 | 3/1995 | Cheng et al. | 437/105 |
| 5,422,489 | 6/1995 | Bhargava | 250/488.1 |
| 5,492,080 | 2/1996 | Ohkawa et al. | 117/108 |
| 5,499,260 | 3/1996 | Takahashi et al. | 372/46 |
| 5,505,928 | 4/1996 | Alivisatos et al. | 423/299 |
| 5,515,393 | 5/1996 | Okuyama et al. | 372/45 |
| 5,525,377 | 6/1996 | Gallagher et al. | 427/512 |
| 5,537,000 | 7/1996 | Alivisatos et al. | 313/506 |
| 5,541,948 | 7/1996 | Krupke et al. | 372/41 |
| 5,565,324 | 10/1996 | Still et al. | 435/6 |
| 5,585,640 | 12/1996 | Huston et al. | 250/483.1 |
| 5,625,456 | 4/1997 | Lawandy | 356/376 |
| 5,674,698 | 10/1997 | Zarling et al. | 435/7.92 |
| 5,721,099 | 2/1998 | Still et al. | 435/6 |
| 5,736,330 | 4/1998 | Fulton | 435/6 |
| 5,747,180 | 5/1998 | Miller et al. | 372/41 |
| 5,751,018 | * 5/1998 | Alivisatos et al. | 257/64 |
| 5,770,299 | 6/1998 | Dannenhauer et al. | 428/195 |
| 5,789,162 | 8/1998 | Dower et al. | 435/6 |
| 5,985,173 | * 11/1999 | Grey et al. | 252/301.4 R |
| 5,985,353 | 11/1999 | Lawton et al. | 427/2.13 |
| 5,990,479 | 11/1999 | Weiss et al. | 250/307 |
| 6,114,038 | * 9/2000 | Castro et al. | 428/402.24 |

FOREIGN PATENT DOCUMENTS

| | | |
|---|---|---|
| WO 98/36376 | 8/1998 | (WO) . |
| WO 98/46372 | 10/1998 | (WO) . |
| WO 99/19515 | 4/1999 | (WO) . |
| WO 00/27365 | 5/2000 | (WO) . |
| WO 00/27436 | 5/2000 | (WO) . |
| WO 00/28088 | 5/2000 | (WO) . |
| WO 00/28089 | 5/2000 | (WO) . |

OTHER PUBLICATIONS

Kortan et al., "Nucleation and Growth of CdSe on ZnS Quantum Crystallite Seeds, and Vice Versa, In Inverse Micelle Media" *J. Am Chem. Soc.* 112: 1327–1332, 1990.

Murray et al., "Synthesis and Characterization of Nearly Monodisperse CdE (E=S, Se, Te) Semiconductor Nanocrystallites" *J. Am. Chem. Soc.* 115(19):8706–8715, 1993.

Rajh et al., "Synthesis and Characterization of Surface–Modified Colloidal CdTe Quantum Dots" *J. Phys. Chem.* 97:11999–12003, Nov. 1993.

Lawless et al., "Bifunctional Capping of CdS Nanoparticles and Bridging to TiO2" *J. Phys. Chem.* 99:10329–10335, 1995.

Dabbousi et al., "Electroluminescence from CdSe quantum–dot/polymer composites" *Appl. Phys. Lett.* 66(11):1316–1318, Mar. 13, 1995.

Alivisatos, "Perspectives on the Physical Chemistry of Semiconductor Nanocrystals" *J. Phys. Chem.* 1996(100):13226–13239, 1996.

Danek et al., "Synthesis of Luminescent Thin–Film CdSe/ZnSe Quantum Dot Composites Using CdSe Quantum Dots Passivated with an Overlayer of ZnSe" *Chem. Mater.* 8(1):173–180, 1996.

Liz–Marzan et al., "Synthesis of Nanosized Gold–Silica Core–Shell Particles" *Langmuir* 12:4329–4335, 1996.

Matsumoto et al., "Preparation of Monodisperse CdS Nanocrystals by Size Selective Photocorrosion" *J. Phys. Chem.* 100(32):13781–13785, 1996.

Rogach et al., "Synthesis and characterization of Thiol–Stabilized CdTe Nanocrystals" *Ber. Bunsenges. Phys. Chem.* 100(11):1772–2778, 1996.

Hines et al., "Synthesis and Characterization of Strongly Luminescing ZnS–Capped CdSe Nanocrystals" *J. Phys. Chem.* 100:468–471, Jan. 1996.

Empedocles et al, "Photoluminescence Spectroscopy of Single CdSe Nanocrystallite Quantum Dots" *Phys. Rev. Lett.* 77(18):3873–3876, Oct. 1996.

Nirmal et al., "Fluorescence Intermittency in single Cadmium Selenide Nanocrystals" *Nature* 383:802–804, Oct. 1996.

Gan et al., "Enhanced Photoluminescence and Characterization of Mn–Doped ZnS Nanocrystallites Synthesized in Microemulsion" *Langmuir* 1997(13):6427–6431, 1997.

Empedocles et al., "Quantum–Confined Stark Effect in Single CdSe Nanocrystallite Quantum Dots" *Science* 278:2114–2117, Dec. 1997.

Kuno et al., "The band edge luminescence of surface modified CdSe nanocrystallites: Probing the luminescing state" *J. Chem. Phys.* 106(23):9869–9882, Jun. 1997.

Dabbousi, et al., "(CdSe)ZnS core–shell quantum dots: synthesis and characterization of a size series of highly luminescent nanocrystallites" *J. of Phys. Chem. B* 101(46):9463–9475, Nov. 13, 1997.

Fox et al., "Fluorescence and Redox Activity of Probes Anchored through an Aminotrithiol to Polycrystalline Gold" *Langmuir* 14:816–820, 1998.

Mikulec et al., "Fluorescent semiconductor nanocrystallites derivatized with biomolecules" Amer. Chem.. Soc. Nat'l Meeting, Boston, MA, Aug. 24, 1998.

Lett, "Color–Coding Quantum Dots Debut With Promising Careers In Clinical Diagnostics Field" :1–2, Sep. 25, 1998.

Alivisatos et al., "Semiconductor Clusters, Nanocrystals, and Quantum Dots," *Science*, 271:933–937, 1996.

Alivisatos et al., "Organization of 'nanocrystal molecules' using DNA," *Nature*, 382:609–611, Aug. 15, 1996.

Baldwin et al., "Synthesis of a Small Molecule Combinatorial Library Encoded with Molecular Tags," *J. Am. Chem. Soc.*, 117:5588–5589, May 24, 1995.

Bawendi et al., "Luminescence properties of CdSe quantum crystallites: resonance between interior and surface localized states," *J. Chem. Phys.*, 96(2):946–954, Jan. 15, 1992.

Beverloo et al., "Preparation and Microscopic Visualization of Multicolor Luminescent Immunophosphors," *Cytometry*, 13:561–570, 1992.

Bruchez et al., "Semiconductor Nanocrystals as Fluorescent Biological Labels," *Science*, 281:2013–2016, Sep. 25, 1998.

Bruchez et al., "Semiconductor nanocrystals as fluorescent piological for biology," *Cytometry*, Supplement 9, p. 26, Mar., 1998.

Bruchez et al., "Luminescent Semiconductor Nanocrystals: Intermitten Behavior and Use as Fluorescent Probes," Doctoral Dissertation, University of California, Jul. 13, 1999.

Chan et al., "Quantum Dot Bioconjugates for Ultrasensitive Nonisotopic Detection," *Science*, 281:2016–2018, Sep. 25, 1998.

Chee et al., "Accessing Genetic Information with High–Density DNA Arrays," *Science*, 274(5287):610, Oct. 25, 1996.

Coffer et al., "Characterization of quantum–confined CdS nanocrystallites stabilized by deoxyribonucleic acid (DNA)," *Nanotechnology*, 3:69–76, 1992.

Colvin et al., "Light–emitting diodes made from cadmium selenide nanocrystals and a semiconducting polymer" *Nature*, 370(6488):354–357, Aug. 4, 1994.

Cook, "Scintillation Proximity Assay: A Versatile High–Throughput Screening Technology," *Drug Discovery Today*, 1:287–294, 1997.

Correa–Duarte et al., "Stabilization of CdS semiconductor nanoparticles against photodegradation by silica coating procedure," *Chem. Phys. Lett.*, 286:497–501, Apr. 17, 1998.

Czarnik, "Encoding methods for combinatorial chemistry," *Curr. Opin. Chem. Biol.*, 1(1):60, 1997.

Egner et al., "Tagging in combinatorial chemistry: the use of coloured and fluorescent beads," *Chem. Commun..*, 735–736, Apr. 21, 1997.

Fodor, "Techwire," *Science*, 277(5324):393–395, Jul. 18, 1997.

Gao et al., "Strongly Photoluminescent CdTe Nanocrystals by Proper Surface Modification," *J. Phys. Chem.*, 102:8360–8363, 1998.

Guha et al., "Hybrid organic–inorganic semiconductor–based light–emitting diodes," *J. Appl. Phys.*, 82(8):4126–4128, Oct. 15, 1997.

Jacoby, "Quantum Dots Meet Biomolecules," *C&E News*, 8:, Sep. 28, 1998.

Jarvis et al., "Solution Synthesis and Photoluminescence Studies of Small Crystallites of Cadmium Telluride," *Mat. Res. Soc. Symp. Proc.*, 272:229–234, 1992.

Kagan et al., "Electronic Energy Transfer in CdSe Quantum Dot Solids," *Physical Review Letters*, 76:1517–1520, Feb. 26, 1996.

Kagan et al., "Long–range resonance transfer of electronic excitations in close–packed CdSe quantum–dot solids," *Physical Review Letters*, 54:8633–8643, Sep. 15, 1996.

Lee et al., "Surface Derivatization of Nanocrystalline CdSe Semiconductors," *Mat. Res. Soc. Symp. Proc.*, 452:323–328, 1997.

Mahtab et al., "Protein–sized quantum dot luminescence can distinguish between 'straight', 'bent', and 'kinked' oligonucletides", *J. Am. Chem. Soc.*, 117:9099–9100, Sep. 6, 1995.

Mahtab et al., "Preferential–absorption of a 'kinked' DNA to a newtral curved surface: comparison to and implications for nonspecific DNA–protein interactions," *J. Am. Chem. Soc.*, 118:7028–7032, Jul. 31, 1996.

McGall et al., "Light–directed synthesis of high–density oligonucliotide arrays using semiconductor photoresists," *Proc. Natl. Acad. Sci. USA*, 93:13555–13560, Nov., 1996.

Michael et al., "Randomly Ordered Addressable High–Density Optical Sensor Arrays," *Analytical Chemistry*, 70:1242–1248, Apr. 1, 1998.

Mikulec et al., "Synthesis and Characterization of Highly Luminescent (CdSe)ZnS Quantum Dots," *Materials Research Society Symposium*, 452:359–364, 1997.

Moran, "Radio Frequency Tag Encoded Combinatorial Library Method for the Discovery of Tripeptide–Substituted Cinnamic Acid Inhibitors of the Protein Tyrosine Phosphatase PTP1B," *J. Am. Chem. Soc.*, 117:10787–10788, 1995.

Müllenborn et al., "Characterization of Solution–Synthesized CdTe and HgTe," *Applied Physics*, 56:317–321, 1993.

Murphy et al., "Quantum dots as inorganic DNA–binding proteins," *Mat. Res. Soc. Symp.*, 452:597–600, 1997.

Nicolaou et al., "Radiofrequency Encoded Combinatorial Chemistry," *Ingew. Chem. Int. Ed. Engl.*, 34(20):2289–2291, 1995.

Pehnt et al., "Nanoparticle Precursor Route to Low–Temperature Spray Deposition of CdTe Thin Films," *Appl. Phys. Lett.*, 67(15):2176–2178, Oct. 9, 1995.

Peng et al., "Epitaxial Growth of Highly Luminescent CdSe/CdS Core/Shell Nanocrystals with Photostability and Electronic Accessibility," *J. Am. Chem. Soc.*, 119:7019–7029, Jul. 30, 1997.

Peng et al., "Synthesis and Isolation of a Homodimer of Cadmium Selenide Nanocrystals," *Angewandte Chemie*, 36:145–147, Feb. 3, 1997.

Plunkett et al., "Combinatorial Chemistry and New Drugs," *Scientific American*, 276(4):68–73, Apr. 1997.

Schröck et al., "Multicolor Spectral Karyotyping of Human Chromosomes," *Science*, 273:494–497, Jul. 26, 1996.

Service, "Semiconductor Beacons Light Up Cell Structures," *Science*, 281:1930–1931, Sep. 25, 1998.

Steigerwald et al., "Surface Derivatization and Isolation of Semiconductor Cluster Molecules," *J. Am. Chem. Soc.*, 110:3046–3050, 1988.

Wade, "In the Hunt for Useful Genes, a Lot Depends on 'Snips'", *New York Times*, C1, C5, Aug. 11, 1998.

Wang et al., "Large–Scale Identification, Mapping, and Genotyping of Single–Nucleotide Polymorphisms in the Human Genome," *Science*, 280:1077–1082, May 15, 1988.

Whitesell, "Directionally Aligned Helical Peptides on Surfaces", *Science*, 261:73–75, Jul. 2, 1993.

Winzeler et al., "Direct Allelic Variation Scanning of the Yeast Genome", *Science*, 281:1194–1197, Aug. 21, 1998.

* cited by examiner

WATER-SOLUBLE FLUORESCENT SEMICONDUCTOR NANOCRYSTALS

This application is a continuation-in-part of Ser. No. 09/156,863 entitled "Water-Soluble Luminescent Nanocrystals," filed Sep. 18, 1998, which is incorporated in its entirety, now U.S. Pat. No. 6,251,303. This application is related to the following commonly owned applications, the disclosures of which are incorporated in their entirety by reference: Ser. No. 60/100,947, entitled "Detection of Compounds and Interactions in Biological Systems Using Quantum Dots," filed Sep. 18, 1998; Ser. No. 09/160,454, entitled "Biological Applications of Quantum Dots," filed Sep. 24, 1998; Ser. No. 09/397,436, entitled "Biological Applications of Semiconductor Nanocrystals," filed Sep. 17, 1999; Ser. No. 60/101,046 entitled "Inventory Control" filed Sep. 18, 1998; Ser. No. 09/160,458 entitled "Inventory Control" filed Sep. 24, 1998; and Ser. No. 09/397,432 entitled "Inventory Control" filed Sep. 17, 1999.

This invention was made with U.S. government support under Contract Number 94-00334 awarded by the National Science Foundation. The U.S. government has certain rights in the invention.

FIELD OF THE INVENTION

This invention relates to water-soluble nanocrystalline materials that emit energy over a narrow range of wavelengths. In particular, the invention relates to water-soluble nanocrystals that emit light in the visible and infrared energy range.

BACKGROUND OF THE INVENTION

Semiconductor nanocrystals (also known as Quantum Dot™ particles) whose radii are smaller than the bulk exciton Bohr radius constitute a class of materials intermediate between molecular and bulk forms of matter. Quantum confinement of both the electron and hole in all three dimensions leads to an increase in the effective band gap of the material with decreasing crystallite size. Consequently, both the optical absorption and emission of semiconductor nanocrystals shift to the blue (higher energies) as the size of the nanocrystals gets smaller.

Bawendi and co-workers have described a method of preparing monodisperse semiconductor nanocrystals by pyrolysis of organometallic reagents injected into a hot coordinating solvent (Murray et al. (1993) *J. Am. Chem. Soc.*, 115:8706). This permits temporally discrete nucleation and results in the controlled growth of macroscopic quantities of nanocrystals. Size-selective precipitation of the crystallites from the growth solution can provide crystallites with even narrower size distributions. The narrow size distribution of the semiconductor nanocrystals allows the possibility of light emission with narrow spectral linewidths.

In an effort to improve the photoluminescent yield of the semiconductor nanocrystals, the nanocrystal surface has been passivated by reaction of the surface atoms of the nanocrystal with organic passivating ligands, to eliminate energy levels at the surface of the crystallite that lie within the energetically forbidden gap of the bulk interior. These surface energy states act as traps for electrons and holes that degrade the luminescence properties of the material. Such passivation produces an atomically abrupt increase in the chemical potential at the interface of the semiconductor and passivating layer (see, Alivisatos (1996) *J. Phys. Chem.* 100:13226). Murray et al. (1993), supra, describes CdSe nanocrystals capped with organic moieties such as tri-n-octyl phosphine (TOP) and tri-n-octyl phosphine oxide (TOPO) with quantum yields as high as 20% in organic solvents such as toluene (see, also, doctoral thesis of Christopher Murray, "Synthesis and Characterization of II-VI Quantum Dots and Their Assembly into 3-D Quantum Dot Superlattices" (1995) Massachusetts Institute of Technology; and Kuno et al. (997) *J. Phys. Chem.* 106(23):9869).

Although semiconductor nanocrystals prepared as described by Bawendi and co-workers exhibit near monodispersity, and hence, high color selectivity, the luminescence properties of the material is process dependent. The stability of the photoluminescent property of the nanocrystal is a function of the nature of the passivating species coating the outer surface of the nanocrystal. Known organically coated nanocrystals are not robust and exhibit degradation of photoluminescent yield in solution. This is likely due to dissociation of the passivating layer from the surface of the nanocrystal or degradation of the passivating layer resulting in degradation of the semiconductor surface.

Passivation of semiconductor nanocrystals using inorganic materials also has been reported. Particles passivated with an inorganic coating are more robust than organically passivated particles and have greater tolerance to processing conditions necessary for their incorporation into devices. Previously reported inorganically passivated semiconductor nanocrystal particle structures include CdS-capped CdSe and CdSe-capped CdS (Than et al. (1996) *J. Phys. Chem.* 100:8927); ZnS grown on CdS (Youn et al. (1988) *J. Phys. Chem.* 92:6320); ZnS on CdSe and the inverse structure (Kortan et al. (1990) *J. Am. Chem. Soc.* 112:1327); ZnS-capped CdSe nanocrystals (Hines et al. (1996) *J. Phys. Chem.* 100:468; ZnSe-capped CdSe nanocrystals (Danek et al. (1996) *Chem. Malerials* 8:173); and $SiO_2$ on Si (Wilson et al. (1993) Science 262:1242).

Kortan et al. (1990), supra, describes a ZnS capped-CdSe nanoparticle that has a layer of thiolphenyl groups bound to the outer surface. The thiolphenyl groups were used to passivate the surface and to allow the clusters to be isolated in powder form. Lawless et al. (1995) *J. Phys. Chem.* 99:10329 reported the preparation of CdS semiconductor nanocrystals capped with bifunctional mercaptocarboxylic acids $HS(CH_2)_n COOH$, wherein n is 1–3. $TiO_2$ particles were attached to the CdS nanocrystals through the functional carboxylic acid group of the bifunctional capping moiety in order to promote interparticle electron transfer between dissimilar semiconductor particles.

The semiconductor nanocrystals described above are soluble or dispersible only in organic solvents, such as hexane or pyridine. Many applications that rely on the fluorescent emission of the semiconductor nanocrystals require that the semiconductor nanocrystals be water-soluble.

Many reported water-soluble semiconductor nanocrystals suffer from significant disadvantages that limit their wide applicability. For example, Spanhel et al. (1987) *J. Am. Chem. Soc.* 109:5649, discloses a $Cd(OH)_2$-capped CdS sol; however, the photoluminescent properties of the sol were pH dependent. The sol could be prepared only in a very narrow pH range (pH 8–10) and exhibited a narrow fluorescence band only at a pH of greater than 10. Such pH dependency greatly limits the usefulness of the material; in particular, it is not appropriate for use in biological systems.

Other groups have replaced the organic passivating layer of the semiconductor nanocrystal with water-soluble moieties; however, the resultant derivatized semiconductor nanocrystals are not highly luminescent. Short chain thiols such as 2-mercaptoethanol and 1-thio-glycerol have been used as stabilizers in the preparation of water-soluble CdTe nanocrystals. See, Rogach et al. (1996) *Ber. Bunsenges. Phys. Chem.* 100:1772 and Rajh et al. (1993) *J. Phys. Chem.* 97:11999. Other more exotic capping compounds have been reported with similar results. See, Coffer et al. (1992) *Nanotechnology* 3:69 which describes the use of deoxyribonucleic acid (DNA) as a capping compound. In all of these systems, the coated semiconductor nanocrystals were not stable and photoluminescent properties degraded with time.

The unavailability of aqueous suspensions or solutions of semiconductor nanocrystals with sharp photoluminescent emissions limits their application in a variety of water-based applications, such as biological applications. In addition, aqueous solutions can often be very aggressive chemical systems and many of the known water-soluble semiconductor nanocrystal systems degrade, mainly by photoanodic decomposition at the semiconductor surface interface, during long exposure times in water.

Thus, there remains a need for water-soluble semiconductor nanocrystals that can be prepared as stable, robust suspensions or solutions in aqueous media. There is also a need for water-soluble semiconductor nanocrystals capable of energy emission with high quantum efficiencies, which possess a narrow particle size (and hence with narrow photoluminescence spectral range).

SUMMARY OF THE INVENTION

It is a primary object of the invention to address the aforementioned needs in the art.

It is another object of the invention to provide water-soluble semiconductor nanocrystals that overcome the limitations of the prior art and that exhibit high quantum yields with photoluminescence emissions of high spectral purity.

It is yet a further object of the present invention to provide a semiconductor nanocrystal that is readily soluble in aqueous systems and that demonstrates chemical and electronic stability therein.

It is yet a further object of the invention to provide a water-soluble semiconductor nanocrystal derivatized to provide linking or coupling capability.

In one aspect of the invention, a water-soluble semiconductor nanocrystal capable of energy emission is provided. The nanocrystal includes a semiconductor nanocrystal core having a selected band gap energy overcoated with a shell layer of a material having a band gap energy greater than that of the core and with appropriate band offsets. The water-soluble nanocrystal further comprise an outer layer at the outer surface of the overcoating layer. The outer layer includes a molecule having at least one linking group for attachment of the molecule to the overcoating layer and at least one hydrophilic group optionally spaced apart from the linking group by a hydrophobic region sufficient to minimize electron charge transfer across the hydrophobic region.

The outer layer of the nanocrystal can comprise an organic molecule. The organic molecule can be comprised of moieties selected to provide solubility in an aqueous medium, such as a long chain hydrocarbon terminating in a moiety having affinity for an aqueous medium, and a moiety that demonstrates an affinity to the semiconductor nanocrystal surface. The affinity for the nanocrystal surface promotes coordination of the organic molecule to the semiconductor nanocrystal outer surface and the moiety with affinity for the aqueous medium stabilizes the semiconductor nanocrystal suspension.

In one preferred embodiment, the molecule has structural formula (I)

(I)

and salts thereof, wherein: $X^1$ is N, P or O=P; n is greater than or equal to 6; and z and y are selected to satisfy the valence requirements of $X^1$.

In other preferred embodiments, the molecule has structural formula (II)

(II)

wherein: X and X' are the same or different and are selected from the group of S, N, P or O=P; Y is a hydrophilic moiety; and Z is absent or a hydrophobic region having a backbone of at least six atoms. X and X' can include other substituents to satisfy the valence requirements, such as for example, amines, thiols, phosphines and phosphine oxides, substituted by hydrogen or other organic moieties. In addition, the atoms bridging X and X' can be selected to form a 5-membered to 8-membered ring upon coordination to the semiconductor surface. The bridging atoms are typically carbon, but can be other elements, such as oxygen, nitrogen, and sulfur. Y can be any charged or polar group, such as a carboxylate, a sulfonates, a phosphate, a polyethylene glycol or other polyol and an ammonium salt, e.g., carboxylate ($-CO_2^-$), sulfonate ($SO_3^-$), hydroxide ($-OH$), alkoxides, ammonium salts ($-NH_4^+$), and phosphate ($-PO_4^{-2}$) and phosphonate ($-PO_3^{-2}$), and the like. Z is typically an alkyl group or alkenyl group, but can also include other atoms, such as carbon and nitrogen. Z can be further modified as described herein to provide attractive interactions with neighboring ligands.

In yet another preferred embodiment, the molecule has structural formula (III):

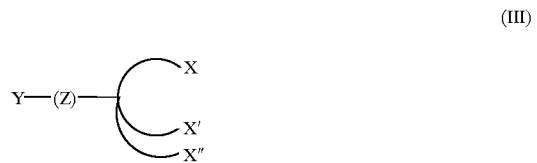
(III)

wherein: X, X' and X" are the same or different and are selected from the group of S, N, P or O=P; Y is a hydrophilic moiety; and Z is a hydrophobic region having a backbone of at least six atoms. X, X' and X" can include other substituents in order to satisfy the valence requirements, such as for example, amines, thiols, phosphines and phosphine oxides, substituted by hydrogen or other organic moieties. In addition, the atoms bridging X and X', X and X", or X' and X" are each can be selected to form a 5-membered to 8-membered ring upon coordination to the semiconductor surface. The bridging atoms are typically carbon, but can be other elements, such as oxygen, nitrogen, and sulfur. Y can be any charged or polar group, such as a carboxylate, a sulfonate, a phosphate, a polyethylene glycol or other polyol and an ammonium salt, e.g., carboxylate ($-CO_2^-$), sulfonate ($-SO_3^-$), hydroxide ($-OH$), alkoxides, ammonium salts ($-NH_4^+$), phosphate ($-PO_4^{-2}$), phosphonate ($-PO_3^{-2}$), and the like. Z is typically an alkyl group or alkenyl group, but can also include other atoms, such as carbon and nitrogen. Z can be further modified as described herein to provide attractive interactions with neighboring ligands.

In other preferred embodiments, the molecule has structural formula (IV):

wherein:

$R^1$ is selected from the group consisting of heteroalkyl, heteroalkenyl, heteroalkynyl, —OR, —SR, —NHR, —NR'R", —N(O)HR, —N(O)R'R", —PHR, —PR'R", —P(NR'R")NR'R", —P(O)R'R", —P(O)(NR'R") NR'R", —P(O)(OR')OR", —P(O)OR, —P(O)NR'R", —P(S)(OR')OR", and —P(S)OR, wherein R, R'and R"are independently selected from the group consisting of H, a branched or unbranched alkyl, a branched or unbranched alkenyl, a branched or unbranched alkynyl, a branched or unbranched heteroalkyl, a branched or unbranched heteroalkenyl and a branched or unbranched heteroalkynyl, with the proviso that when a is greater than 1 the $R^1$ groups can be the same or different or can be linked to form a six-, seven-, eight-, nine- or ten-membered cycloalkyl, cycloalkenyl, heterocyclic, aryl, heteroaryl, or a six- to thirty-membered crown ether or heterocrown ether;

$R^2$ is selected from a bond (i.e., $R^2$ is absent), a branched or unbranched alkylene, a branched or unbranched alkenylene, a branched or unbranched heteroalkylene, a branched or unbranched heteroalkenylene, cycloalkyl, cycloalkenyl, cycloalkynyl, heterocyclic, aryl and heteroaryl;

$R^3$ is selected from a branched or unbranched alkylene, a branched or unbranched alkenylene, a branched or unbranched heteroalkylene, a branched or unbranched heteroalkenylene, cycloalkyl, cycloalkenyl, cycloalkynyl, heterocyclic, aryl and heteroaryl;

$R^4$ is selected from the group consisting of hydrogen, a carboxylate, a thiocarboxylate, an amide, an imide, a hydrazine, a sulfonate, a sulfoxide, a sulfone, a sulfite, a phosphate, a phosphonate, a phosphonium, an alcohol, a thiol, an amine, an ammonium, an alkyl ammonium, a nitrate, a sugar moiety, and a five-, six-, seven-, eight-, nine- or ten-membered cycloalkenyl, cycloalkynyl, heterocyclic, aryl, or heteroaryl;

a is 1, 2, 3 or 4;

b is 0, 1, 2 or 3;

c is 0, 1, 2 or 3; and d is 0, 1, 2 or 3, wherein when d is 2 or 3 the $R^3$ groups can be the same or different or can be linked together to form a five-, six-, seven-, eight-, nine- or ten-membered cycloalkyl, cycloalkenyl, heterocyclic, aryl, or heteroaryl.

Preferably, $R^1$ is a thiol (e.g., —SH), a phosphine, a phosphine oxide, or an amine (e.g., —NH2, —NHR or —NRR').

Preferably, $R^2$ contains between 6 and 20 atoms. More preferably, $R^2$ is a linear alkylene, alkenylene, alkynylene, heteroalkylene, heteroalkenylene or heteroalkynylene containing 6,7,8,9, 10, 11, 12, 13, 14, 15, 16, 17, 18, 19 or 20 atoms, or a cycloalkyl or heterocyclic containing 5 or 6 atoms.

Preferably, when b is 1, 2 or 3, $R^3$ contains between 6 and 20 atoms. More preferably, $R^3$ is a linear alkylene, alkenylene, alkynylene, heteroalkylene, heteroalkenylene or heteroalkynylene containing 6, 7, 8, 9, 10, 11, 12, 13, 14, 15, 16, 17, 18, 19 or 20 atoms, or a cycloalkyl or heterocyclic containing 5 or 6 atoms.

Preferably, $R^4$ is a carboxylate (—COO$^-$), a phosphonate (—PO$_3^-$) a sulfonate (—SO$_3^-$) or an ammonium (—N$^+$HRR$^1$).

In yet another embodiment of the invention, the molecule has structural formula (V):

wherein pendant groups $R^1$ and $R^4$ and the $R^2$ moiety are as defined above, $X^2$ and $Y^2$ are the same or different and are mer units selected from the group consisting of acrylate, styrene, imide, acrylamide, ethylene, vinyl, diacetylene, phenylene-vinylene, amino acid, sugar, sulfone, pyrrole, imidazole, thiophene and ether, and m' and n' are selected in relation to the number of available coordinating sites on the surface of the semiconductor nanocrystal. It is desirable that m be no greater than the number of available coordinating sites and preferably no greater than about one-fourth of available coordinating sites. In particular, m' is in the range of about 3 to about 100. The value of n' is typically chosen to be commensurate with the value for m'. Thus, it is desirable that n' be no greater than the number of available coordinating sites and preferably no greater than about one-fourth of available coordinating sites. In particular, n' is in the range of about 3 to 100. The molecule can be a block copolymer, wherein a first block is provided that includes a pendant group capable of functioning as a linking moiety, Y. A second block is provided that includes a pendant group capable of functioning as a hydrophilic group, X. The polymer block serves as a hydrophilic region. In preferred embodiment, the molecule has the formula,

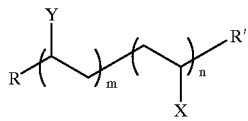

wherein the Xs are the same or different and are elements selected from the group of S, N, P or O=P; and the Ys are the same or different and are hydrophilic moieties, such as carboxylates, sulfonates, phosphates, phosphonates, polyethylene glycol, ammonium salt, and the like. X can include other substituents in order to satisfy the valence requirements, such as for example, amines, thiols, phosphine and phosphine oxides, substituted by hydrogen or other organic moieties. The terminal groups R and R' can be any moiety, including hydrogen. In particular, it is desirable for R to be a polar moiety due to its proximity to the hydrophilic block. Similarly, it is desirable for R' to be a non-polar moiety due to its proximity to the hydrophobic block. m and n are selected in relation to the number of available coordinating sites on the surface of the semiconductor nanocrystal. It is desirable that m be no greater than the number of available coordinating sites and preferably no greater than one-fourth of available coordinating sites. In typical applications, m is in the range of about 3 to 100. The value of n is typically chosen to be commensurate with the value for m. Thus, it is desirable that n be no greater than the number of available coordinating sites and preferably no greater than one-fourth of available coordinating sites. In typical applications, n is in the range of about 3 to 100.

Although not wishing to be bound by theory, the inventors believe that coordination of the molecule having structural formula (IV) to the overcoated nanocrystal occurs between surface moieties on the nanocrystal and the $R^1$ moiety of the molecule.

In another preferred embodiment, the water-solubilizing outer layer can comprise a homogeneous population of molecules having structural formula (I), (II), (III), (IV) or (V), a mixed population of molecules any individual structural formula, i.e., a mixed population of molecules all of which have structural formula (I), (II), (III), (IV) or (V), or a mixed population of molecules which have a combination of two or more of structural formulas (I), (II), (III), (IV) and (V).

In another aspect of the invention, a water-soluble semiconductor nanocrystal is provided in which the water solubilizing layer is a bilayer, having a first layer of the bilayer having affinity for the overcoating layer and a second layer of the bilayer having a hydrophobic region adjacent to the first layer and terminating in a hydrophilic group. The bilayer can include a coordinating lyophilic molecule used in the manufacture of the semiconductor nanocrystal as the first layer and a surfactant as the second layer.

These and other embodiments of the present invention will readily occur to those of ordinary skill in the art in view of the disclosure herein.

BRIEF DESCRIPTION OF THE DRAWING

The invention is described with reference to the figures, which are presented for the purpose of illustration only, and in which.

DETAILED DESCRIPTION OF THE INVENTION

Definitions and Nomenclature

Figure 1:
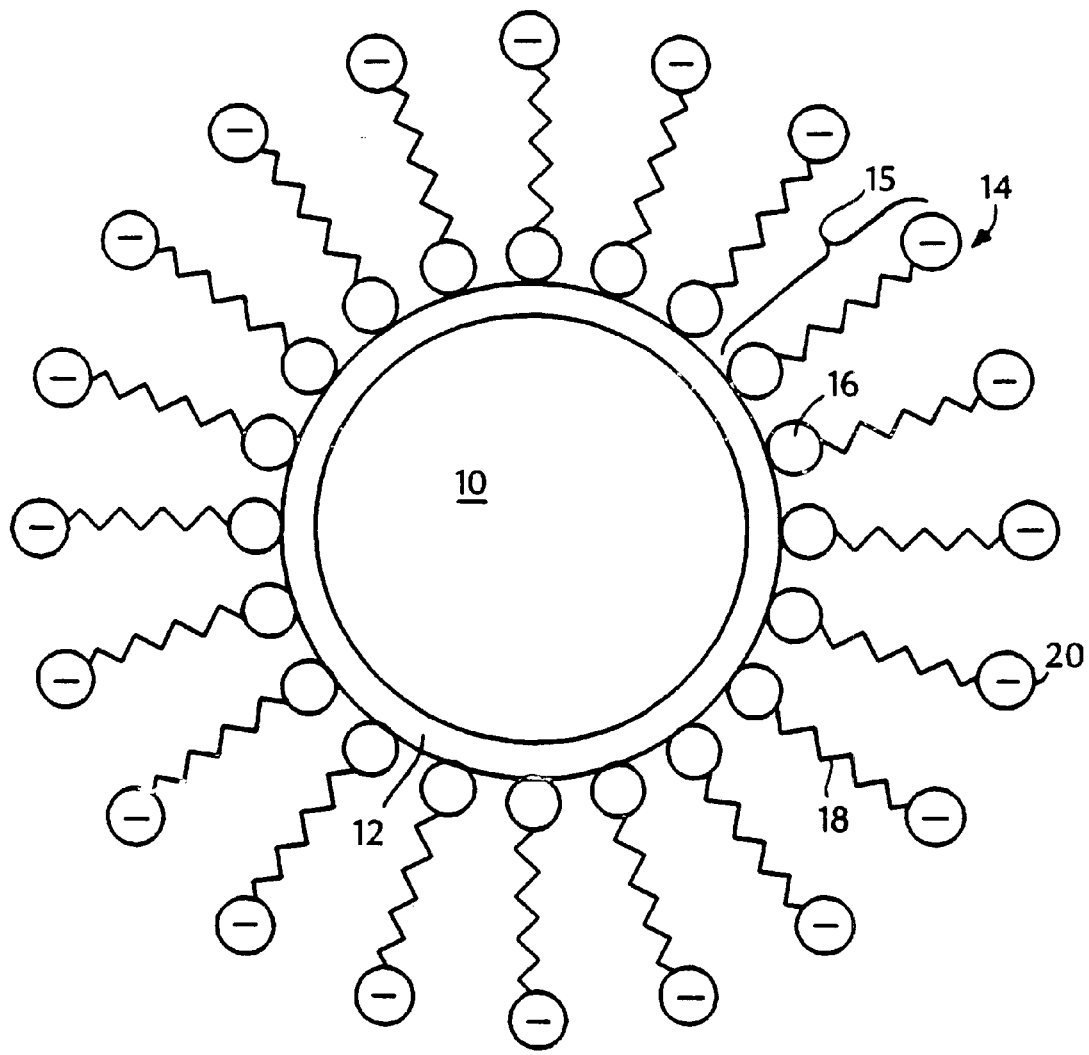
FIG. 1 is a schematic illustration of the water-soluble nanocrystal of the invention.

Before the present invention is disclosed and described in detail, it is to be understood that this invention is not limited to specific assay formats, materials or reagents, as such may, of course, vary. It is also to be understood that the terminology used herein is for the purpose of describing particular embodiments only and is not intended to be limiting.

It must be noted that, as used in the specification and the appended claims, the singular forms "a," "an" and "the" include plural referents unless the context clearly dictates otherwise. Thus, for example, reference to "a nanocrystal" includes more than one nanocrystal, reference to "an outer layer" includes more than one such outer layer, and the like.

In this specification and in the claims that follow, reference will be made to a number of terms that shall be defined to have the following meanings:

"Quantum dot™ particles" are a semiconductor nanocrystal with size-dependent optical and electronic properties. In particular, the band gap energy of a semiconductor nanocrystal varies with the diameter of the crystal. "Semiconductor nanocrystal" includes, for example, inorganic crystallites between about 1 nm and about 1000 nm in diameter, preferably between about 2 nm and about 50 nm, more preferably about 5 nm to about 20 nm (such as about 5, 6, 7, 8, 9, 10, 11, 12, 13, 14, 15, 16, 17, 1 8, 19, or 20 nm) that includes a "core" of one or more first semiconductor materials, and which can be surrounded by a "shell" of a second semiconductor material. A semiconductor nanocrystal core surrounded by a semiconductor shell is referred to as a "core/shell" semiconductor nanocrystal. The surrounding "shell" material will preferably have a bandgap greater than the bandgap of the core material and can be chosen so to have an atomic spacing close to that of the "core" substrate. The core and/or the shell can be a semiconductor material including, but not limited to, those of the group II–VI (e.g., ZnS, ZnSe, ZnTe, CdS, CdSe, CdTe, HgS, HgSe, HgTe, MgTe and the like) and III–V (e.g., GaN, GaP, GaAs, GaSb, InN, InP, InAs, InSb, AlAs, AlP, AlSb, AlS, and the like) and IV (e.g., Ge, Si, Pb and the like) materials, and an alloy thereof, or a mixture, including ternary and quaternary mixtures, thereof.

A semiconductor nanocrystal is, optionally, surrounded by a "coat" of an organic capping agent. The organic capping agent can be any number of materials, but has an affinity for the semiconductor nanocrystal surface. In general, the capping agent can be an isolated organic molecule, a polymer (or a monomer for a polymerization reaction), an inorganic complex, and an extended crystalline structure. The coat is used to convey solubility, e.g., the ability to disperse a coated semiconductor nanocrystal homogeneously into a chosen solvent, functionality, binding properties, or the like. In addition, the coat can be used to tailor the optical properties of the semiconductor nanocrystal. "Quantum yield" as that term is used herein, means the ratio of photons emitted to that absorbed, e.g., the photoluminescence quantum yield.

In other embodiments of the invention, the coated nanocrystal is characterized in that the nanocrystal exhibits less than a 10% rms (root mean square) and preferably less than 5% rms deviation in diameter of the core. Thus, the phrase "monodisperse particles" includes a population of particles wherein the population of particles deviate less than 10% rms in diameter and preferably less than 5% rms. The nanocrystal in an aqueous environment preferably exhibits photoluminescence having quantum yields of greater than 10%, and most preferably in the range of about 10 to 30%.

The term "alkyl" as used herein includes reference to a branched or unbranched saturated hydrocarbon group of 1 to 100 carbon atoms, such as methyl, ethyl, n-propyl, isopropyl, n-butyl, isobutyl, t-butyl, octyl, decyl, tetradecyl, hexadecyl, eicosyl, tetracosyl and the like, as well as cycloalkyl groups such as cyclopentyl, cyclohexyl and the like. The term "lower alkyl" includes an alkyl group of 1 to 20 carbon atoms, preferably 6 to 20 carbon atoms.

The term "alkylene" as used herein includes reference to a di-functional saturated branched or unbranched hydrocarbon chain containing from 1 to 100 carbon atoms, and includes, for example, methylene (—$CH_2$—), ethylene (—$CH_2$—$CH_2$—), propylene (—$CH_2$—$CH_2$—$CH_2$—), 2-methylpropylene (—$CH_2$—CH($CH_3$)—$CH_2$—), hexylene (—$(CH_2)_6$—), and the like. "Lower alkylene" includes an alkylene group of 1 to 20, more preferably 6 to 20, carbon atoms.

The term "alkenyl" as used herein includes reference to a branched or unbranched hydrocarbon group of 2 to 100 carbon atoms containing at least one carbon-carbon double bond, such as ethenyl, n-propenyl, isopropenyl, n-butenyl, isobutenyl, t-butenyl, octenyl, decenyl, tetradecenyl, hexadecenyl, eicosenyl, tetracosenyl and the like. The term "lower alkenyl" includes an alkenyl group of 2 to 20 carbon atoms, preferably 6 to 20 carbon atoms, containing one —C=C— bond.

The term "alkenylene" includes reference to a difunctional branched or unbranched hydrocarbon chain containing from 2 to 100 carbon atoms and at least one carbon-carbon double bond. "Lower alkenylene" includes an alkenylene group of 2 to 20, more preferably 6 to 20, carbon atoms, containing one carbon-carbon double bond.

The term "alkynyl" as used herein includes reference to a branched or unbranched hydrocarbon group of 2 to 100 carbon atoms containing at least one C≡C bond, such as ethynyl, n-propynyl, isopropynyl, n-butynyl, isobutynyl, t-butynyl, octynyl, decynyl and the like. Preferred alkynyl groups herein contain 6 to 20 carbon atoms. The term "lower alkynyl" includes an alkynyl group of 2 to 10 carbon atoms, and one C≡C bond.

The term "alkynylene" includes reference to a difunctional branched or unbranched hydrocarbon chain containing from 2 to 100 carbon atoms and at least one carbon-carbon triple bond. "Lower alkynylene" includes an alkynylene group of 2 to 10 carbon atoms, containing one C≡C bond.

Optionally, an alkyl, alkylene, alkenyl, alkenylene, alkynyl or alkynyl chain can contain 1 to 6 linkages selected from the group consisting of O—, —S— and —NR— wherein R is hydrogen, lower alkyl or lower alkenyl.

The terms "heteroalkyl," "heteroalkylene," "heteroalkenyl," "heteroalkenylene," "heteroalkynyl" and "heteroalkynylene" include reference to alkyl, alkylene, alkenyl, alkenylene, alkynyl and alkynylene groups, respectively, in which one or more of the carbon atoms have been replaced with, e.g., nitrogen, sulfur or oxygen atoms.

"Alkoxy" includes reference to the group —O—R, wherein R is an alkyl radical as defined above. Examples of an alkoxy radical include, but are not limited to, methoxy, ethoxy, isopropoxy and the like.

"Alkylamino" includes reference to a radical —NHR, wherein R is an alkyl radical as defined above. Examples of alkylamino radicals include, but are not limited to, methylamino, (1-ethylethyl)amino, and the like.

"Alkylthio" includes reference to a radical —R where R is an alkyl radical as defined above. Examples of alkylthio radicals include, but are not limited to, methylthio, butylthio, and the like.

"Dialkylamino" includes reference to a radical —NR'R", wherein R' and R" are each independently alkyl radicals as defined above. Examples of dialkylamino radicals include, but are not limited to, dimethylamino, methylethylamino, diethylamino, di(1-methylethyl)amino, and the like.

"Hydroxyalkyl" includes reference to an alkyl radical as defined above, substituted with one or more hydroxy groups. Examples of hydroxyalkyl radicals include, but are not limited to, hydroxymethyl, 2-hydroxyethyl, 2-hydroxypropyl, 3-hydroxypropyl, 2-hydroxybutyl, 3-hydroxybutyl, 4-hydroxybutyl, 2,3-dihydroxypropyl, 1-(hydroxymethyl)-2-hydroxyethyl, 2,3-dihydroxybutyl, 3,4-dihydroxybutyl, and 2-(hydroxymethyl)-3-hydroxypropyl, and the like.

The term "acyl" as used herein includes reference to an alkyl group bound through a —(CO)— linkage. The term "lower acyl" includes an acyl group in which the alkyl group bound through the carbonyl linkage is a lower alkyl group.

The term "sugar moiety" includes reference to monosaccharides, disaccharides, polysaccharides, and the like. The term "sugar" includes those moieties which have been modified, e.g., wherein one or more of the hydroxyl groups are replaced with halogen, alkoxy moieties, aliphatic groups, or are functionalized as ethers, amines, or the like. Examples of modified sugars include: those which contain a lower alkoxy group in place of a hydroxyl moiety, i.e., α- or β-glycosides such as methyl α-D-glucopyranoside, methyl β-D-glucopyranoside, and the like; those which have been reacted with amines, i.e., N-glycosylamines or N-glycosides such as N-(α-D-glucopyranosyl)methylamine; those containing acylated hydroxyl groups, typically from 1 to 5 lower acyl groups; those containing one or more carboxylic acid groups, e.g., D-gluconic acid or the like; and those containing free amine groups such as D-glucosamine, D-galactosamine, N-acetyl-D-glucosamine or the like. Examples of preferred saccharides are glucose, galactose, fructose, ribose, mannose, arabinose, and xylose. Examples of polysaccharides is dextran and cellulose.

"Aryl" includes reference to a monovalent aromatic hydrocarbon radical consisting of one or more fused rings in which at least one ring is aromatic in nature, which can optionally be substituted with one or more of the following substituents: hydroxy, cyano, alkyl, alkoxy, thioalkyl, halo, haloalkyl, hydroxyalkyl, nitro, amino, alkylamino, and dialkylamino, unless otherwise indicated.

"Heteroaryl" includes reference to a monovalent aromatic carbocyclic radical having one or more rings incorporating one, two or three heteroatoms within the ring (chosen from nitrogen, oxygen, or sulfur) which can optionally be substituted with one or more of the following substituents: hydroxy, cyano, alkyl, alkoxy, thioalkyl, halo, haloalkyl, hydroxyalkyl, nitro, amino, and alkylamino and dialkylamino, unless otherwise indicated.

"Cycloalkyl" includes reference to a monovalent saturated carbocyclic radical consisting of one or more rings, which can optionally be substituted with one or more of the following substituents: hydroxy, cyano, alkyl, alkoxy, thioalkyl, halo, haloalkyl, hydroxyalkyl, nitro, amino, alkylamino and dialkylamino, unless otherwise indicated.

"Cycloalkenyl" includes reference to a monovalent unsaturated carbocyclic radical consisting of one or more rings and containing one or more carbon-carbon double bonds, which can optionally be substituted with one or more of the following substituents: hydroxy, cyano, alkyl, alkoxy, thioalkyl, halo, haloalkyl, hydroxyalkyl, nitro, amino, alkylamino and dialkylamino, unless otherwise indicated.

"Cycloalkynyl" includes reference to a monovalent unsaturated carbocyclic radical consisting of one or more rings and containing one or more carbon-carbon triple bonds, which can optionally be substituted with one or more of the following substituents: hydroxy, cyano, alkyl, alkoxy, thioalkyl, halo, haloalkyl, hydroxyalkyl, nitro, amino, alkylamino and dialkylamino, unless otherwise indicated.

"Heterocyclic" includes reference to a monovalent saturated carbocyclic radical, consisting of one or more rings, incorporating one, two or three heteroatoms (chosen from nitrogen, oxygen or sulfur), which can optionally be substituted with one or more of the following substituents: hydroxy, cyano, alkyl, alkoxy, thioalkyl, halo, haloalkyl, hydroxyalkyl, nitro, amino, alkylamino and dialkylamino, unless otherwise indicated.

The term "crown ether" includes reference to a saturated unbranched heterocyclic molecule, mono-, di-, tri-valent or higher (e.g., 4, 5, 6, 7, or 8) multivalent radical, Crown ethers are typically referred to as "x crown y" or "xCy" wherein x represents the total number of atoms in the molecule and y represents the number of heteroatoms in the molecule. Thus, for example, 12 crown 4 is a crown ether containing 12 atoms, 4 of which are heteroatoms and 1 8C6 is a crown ether containing 18 atoms, 6 of which are heteroatoms. Preferred heteroatoms are O, S and N, and in any particular crown ether the heteroatoms can be the same or different. A "heterocrown ether" is a crown ether in which the heteroatoms are different. Preferred crown ethers are six- to thirty-membered crown or heterocrown ethers, more preferred are 8C4, 9C3, 12C4, 15C5, 18C6 and 20C8, and even more preferred are 12C4 and 18C6.

"Optional" or "optionally" means that the subsequently described event or circumstance may or may not occur, and that the description includes instances where said event or circumstance occurs and instances where it does not. For example, the phrase "optionally substituted alkylene" means that an alkylene moiety may or may not be substituted and that the description includes both unsubstituted alkylene and alkylene where there is substitution, and the like.

The present invention is directed to water-soluble semiconductor nanocrystals that are highly luminescent and stable in aqueous solutions. The nanocrystal is represented schematically in FIG. 1. A semiconductor nanocrystal 10 is coated with an outer layer 14 that renders the crystal water-soluble. The outer layer 14 further is selected to maintain the luminescent properties of the nanocrystal and to improve the robustness of the nanocrystal in aqueous solutions. An optional overcoating layer 12 can be used to coat the semiconductor nanocrystal before application of the outer layer 14. The outer layer includes a molecule 15 having at least one linking group 16 for attachment of the molecule to the overcoating layer and at least one hydrophilic group 20 spaced apart from the linking group by a hydrophobic region 18 sufficient to prevent electron charge transfer across the hydrophobic region. Note that the hydrophilic group 20 denoted for the sake of convenience as a negative charge in FIG. 1; however, the group can be positively charged or polar neutral.

The nanocrystal includes a semiconductor nanocrystal that demonstrates quantum confinement effects in their luminescent properties. These nanocrystals are known as "Quantum Dot™ particles". When semiconductor nanocrystals are illuminated with a primary energy source, a secondary emission of energy occurs of a frequency that corresponds to the band gap of the semiconductor material used in the semiconductor nanocrystal. In quantum confined particles, the band gap is a function of the size of the nanocrystal.

Upon exposure to a light source, the semiconductor nanocrystal emits energy of a wavelength characteristic of its composition and size. The water-soluble layer of the invention can be used with nanocrystals having various combinations of nanocrystal core and overcoating. The invention permits the preparation of a variety of water-soluble nanocrystals having a very narrow particle size distribution and exhibiting improvements in color purity and intensity of their photoluminescent emissions, as well as demonstrating robustness and stability in water-based suspensions and solutions. Most of the II–VI, III–V and group IV semiconductors have been prepared as quantum sized particles and exhibit quantum confinement effects in their physical properties and can be used in the water-soluble nanocrystals of the invention. Exemplary materials suitable for use as semiconductor nanocrystal cores include CdS, CdSe, CdTe, ZnS, ZnSe, ZnTe, MgTe, GaAs, GaP, GaSb, GaN, HgS, HgSe, HgTe, InAs, InP, InSb, InN, AlAs, AlP, AlSb, AlS, PbS, PbSe, Ge, Si, an alloy thereof, or a mixture thereof, including ternary and quaternary mixtures thereof.

The semiconductor nanocrystals are characterized by their uniform nanometer size. By "nanometer" size, it is meant less than about 150 Angstroms (Å), and preferably in the range of 15–150 Å. The nanocrystal also is substantially monodisperse within the broad size range given above. By monodisperse, as that term is used herein, it is meant a colloidal system in which the suspended particles have substantially identical size and shape. For the purposes of the present invention, monodisperse particles mean that at least 60% of the particles fall within a specified particle size range. In preferred embodiments, monodisperse particles deviate less than 10% rms in diameter, and preferably less than 5%. Monodisperse semiconductor nanocrystals have been described in detail in Murray et al. (1993), supra, the Murray thesis (1995), supra, and Kuno et al., supra, which are hereby incorporated in their entireties by reference.

In preferred embodiments, the semiconductor nanocrystal has an overcoating shell layer. At the surface of the semiconductor nanocrystal, surface defects can result in traps for electron or holes that degrade the electrical and optical properties of the semiconductor nanocrystal. An insulating layer at the surface of the semiconductor nanocrystal provides an atomically abrupt jump in the chemical potential at the interface that eliminates energy states that can serve as traps for the electrons and holes. This results in higher efficiency in the luminescent process.

Suitable materials for the overcoating shell layer include semiconductors having a higher band gap energy than the semiconductor nanocrystal. In addition to having a band gap energy greater than the semiconductor nanocrystals, suitable materials for the overcoating shell layer should have good conduction and valence band offset with respect to the semiconductor nanocrystal. Thus, the conduction band is desirably higher and the valance band is desirably lower than those of the semiconductor nanocrystal core. Thus, the core can be overcoated with a shell material comprising ZnO, ZnS, ZnSe, ZnTe, CdO, CdS, CdSe, CdTe, MgS, MgSe, GaAs, GaN, GaP, GaAs, GaSb, HgO, HgS, HgSe, HgTe, InAs, InN, InP, InSb, AlAs, AlN, AlP, AlSb, an alloy thereof, or a mixture thereof, including ternary and quaternary mixtures thereof. Preferably, the band gap energy of the overcoating shell is greater than that of the core. For semiconductor nanocrystals that emit energy in the visible (e.g., CdS, CdSe, CdTe, ZnSe, ZnTe, GaP, GaAs) or near IR (e.g., InP, InAs, InSb, PbS, PbSe), a material that has a band gap energy in the ultraviolet regions can be used. Exemplary materials include ZnS, GaN, and magnesium chalcogenides, e.g., MgS, MgSe and MgTe. For semiconductor nanocrystals that emit in the near IR, materials having a band gap energy in the visible, such as CdS or CdSe, can also be used. The overcoating shell layer can include up to eight monolayers of the semiconductor material.

Particularly preferred semiconductor nanocrystals for emission in the visible include $CdX^3$, wherein $X^3$ is S, Se and Te and $ZnY^3$, where $Y^3$ is Se, Te. For those molecules, ZnS is a preferred material for use as the overcoating. For CdTe, ZnSe can be a preferred material for use as the overcoating due to the higher degree of lattice match between the materials. Overcoated nanocrystals that can be used in the present invention are described in Dabbousi et al. (1997) *J. Phys. Chem. B,* 101(46):9463, and Kuno et al., supra; which are hereby incorporated in their entirety by reference.

Most prior art semiconductor nanocrystals are prepared in a coordinating solvent, resulting in the formation of a passivating organic layer on the nanocrystal surface comprised of the organic solvent. The passivated semiconductor nanocrystals thus are readily soluble in organic solvents, such as toluene, chloroform and hexane. The present invention provides a surface-modified particle that is soluble instead in aqueous media. According to the invention, the surface of the semiconductor nanocrystal is coated with an outer layer that stabilizes the semiconductor nanocrystal in aqueous solution. The outer layer includes a molecule having at least one linking moiety that attaches to the surface of the particle and that terminates in at least one hydrophilic moiety. The linking and hydrophilic moieties are optionally spaced apart by a hydrophobic region sufficient to prevent charge transfer across the region. The hydrophobic region also provides a "pseudo-hydrophobic" environment for the nanocrystal and thereby shields it from its aqueous surroundings. To exhibit high quantum efficiency it is desirable for the particles to remain electronically isolated from one another. The outer layer of the invention serves the additional useful purpose of maintaining the desired isolation between individual semiconductor nanocrystals.

The outer layer can be made up of any material that meets the structural and performance criteria stated herein. The material can be organic or inorganic. In preferred embodiments, the molecule is an organic molecule. In some embodiments, the outer layer can be a mixture of two or more different water-solubilizing molecules. In other embodiments, the outer layer can comprise additional molecules selected to provide a desirable attribute to the semiconductor nanocrystal. For example, the outer coating can include molecules having reactive functional groups for reaction with other substrates or molecules.

Suitable linking moieties include molecules having electron pairs available for interaction with the semiconductor surface, such as oxygen (O), sulfur (S), nitrogen (N) and phosphorus (P). Exemplary molecules include electron-donating moieties such as amines, thiols, phosphines, amine oxides, phosphine oxides, and the like. The linking moiety attaches to the semiconductor nanocrystal surface primarily through coordinate bonding of lone electron pairs of the nitrogen, sulfur, oxygen or phosphorous atom of the linking group. Covalent bonding and ionic bonding can also be used to form the interaction of the outer layer with the semiconductor surface.

Figure 2A:
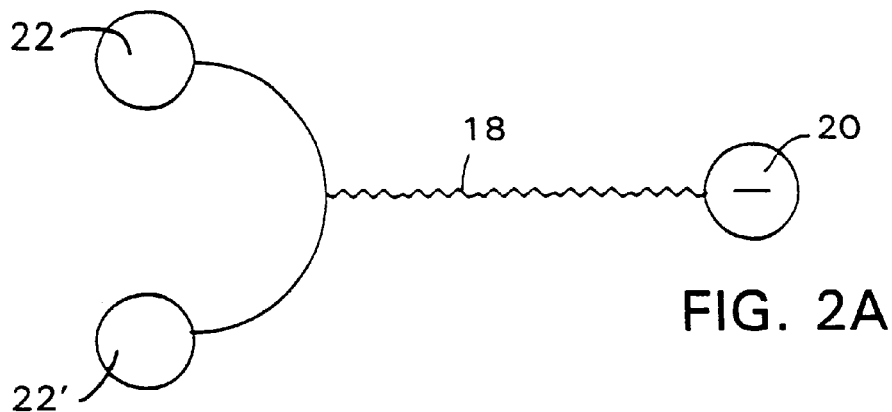
FIGS. 2A, 2B and 2C are schematic illustrations of several alternative embodiments of the water-soluble layer of the nanocrystal.

A molecule having a single linking moiety will result in the formation of an outer layer having water-solubilizing properties; however, it can be desirable for the molecule to comprise a plurality of linking moieties, as illustrated schematically in FIG. 2A. Thus, the molecule can be a bidentate or tridentate ligand having two or more linking groups 22, 22'. Linking groups as described herein above can be used. For example, the molecule can be a derivatized dithiol, diamine, triamine, diphosphine, and the like. The linking groups can be the same or different.

Multidentate ligands provide enhanced stability and robustness to the organic layer and the resulting water-soluble nanocrystal. Without being bound to any particular mode of operation, it is believed that improved stability of the water-soluble nanocrystal is achieved by the increased binding coefficient of the multidentate ligand to the semiconductor surface. Since the organic layer is formed by an exchange reaction with solvated solvent molecules (see below), it follows that the water-solubilizing molecule can also be displaced from the surface of the semiconductor nanocrystal. It has been observed for example that the outer layer can be at least partially removed by dialysis of the water-soluble layer. Use of a multidentate ligand increases the strength of the interaction of the molecule with the semiconductor nanocrystal and decreases the ease of exchange of the organic layer with other coordinating molecules.

Increased stability of the resultant water-soluble semiconductor nanocrystal has been qualitatively observed in the size-selective precipitation of coated semiconductor nanocrystals. Semiconductor nanocrystals that have been overcoated with a bidentate ligand such as lipoic acid, exhibit a four-fold increase in suspension stability over a comparable monodentate ligand-coated molecule.

The hydrophilic moiety can be a polar or charged (positive or negative) group. The polarity or charge of the group provides the necessary hydrophilic interactions with water to provide stable solutions or suspensions of the semiconductor nanocrystal. Exemplary hydrophilic groups include polar groups such as hydroxides (—OH), amines, polyethers, such as polyethylene glycol and the like, as well as charged groups, such as carboxylates (—$CO_2^-$), sulfonates (—$SO_3^-$), phosphates (—$PO_4^{-2}$) and phosphonates (—$PO_3^{-2}$), nitrates, ammonium salts (—$NH_4^+$), and the like.

Figure 2B:
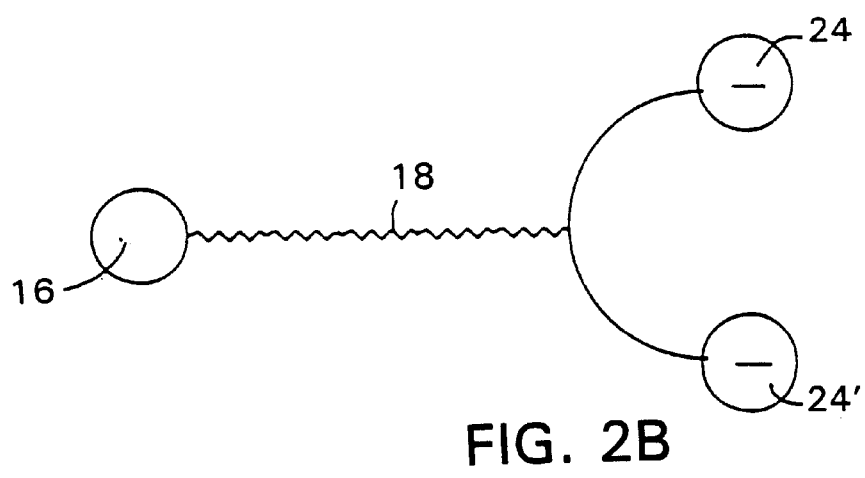
Figure 2C:
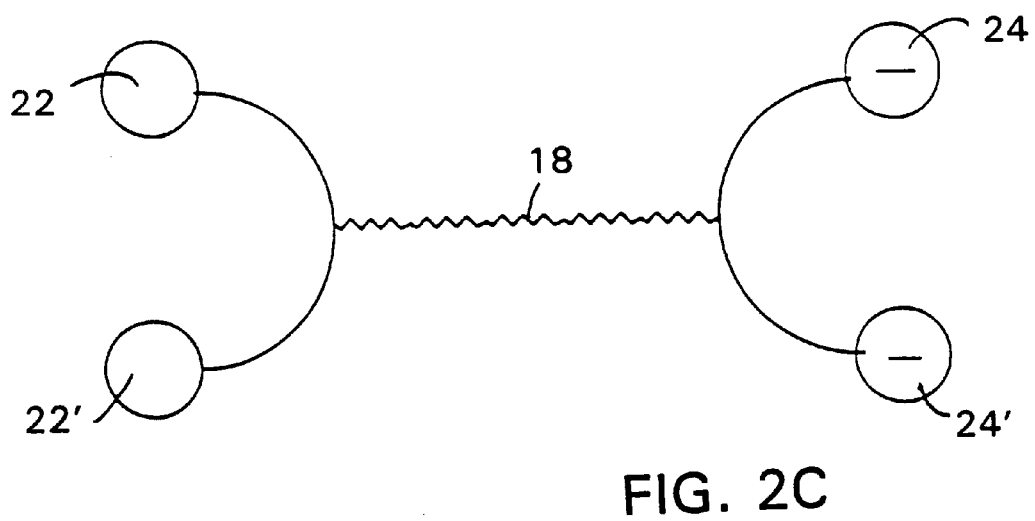

Water solubility has been achieved using molecules having a single hydrophilic group; however, it may be desirable for the molecule to include more than a single hydrophilic moiety, as illustrated schematically in FIG. 2B. FIG. 2B shows a molecule having at least two hydrophilic moieties 24, 24'. The hydrophilic groups can be the same or different. It is also contemplated that the water-solubilizing molecule can include multiple linking groups and hydrophilic groups, as shown in FIG. 2C.

The hydrophobic region is selected to prevent photooxidation of the surface by charge transfer of a hole to the surface either from the core of the semiconductor nanocrystal or the environment. Typical processes include electrolysis of water from the environment with the resultant oxidation of sulfur or selenium (of the semiconductor nanocrystal) to $SO_2$ or $SeO_2$, in instances where the semiconductor nanocrystal or overcoating layer contains S or Se. Transfer of a charge across the layer represents a non-energy emissive pathway for the excited state of the semiconductor and photoluminescence is thereby significantly reduced or quenched.

Prior art surface modifications of semiconductor nanocrystals include capping of CdS nanocrystals with 2-mercaptoethanol, 1-thioglycerol and 3-mercaptopropionic acid. See, Lawless et al., supra, and Rogach et al, supra. These short chain organic molecules do not provide a optimally luminescent, water-soluble semiconductor nanocrystal because the short carbon chain does not provide adequate insulation of the semiconductor nanocrystal against photooxidative processes. Therefore, charge transfer can occur between the semiconductor nanocrystal and either the carboxylate or the aqueous environment. Luminescence is partially quenched and quantum yields are low, i.e., less than 1%, in systems employing short chain organic molecules as a capping layer.

In one embodiment of the invention, the hydrophobic region is a long-chain hydrocarbon moiety, —$(CH_2)_n$—, where n is greater than six and preferably greater than eight. Hydrocarbon moieties wherein n is 11 or 15 have been successfully used in the manufacture of the water-soluble nanocrystal of the invention. There is no upper limit to the hydrocarbon chain length; however, it is recognized that very long hydrocarbon chains might render the nanocrystal undesirably "greasy". The hydrophobic region also can include branching hydrocarbons.

In another embodiment, the hydrophobic region can include a modified hydrocarbon backbone. This modification can be the result of coupling reactions, e.g., carbodiimide coupling, used to increase the length of the hydrophobic backbone. Alternatively, non-carbon atoms can be introduced into the backbone to improve the attractive interaction of the water-solubilizing ligand with neighboring molecules.

The backbone also can be modified to include pendant groups that are attractive to neighboring hydrophobic regions through forces such as van der Waals attraction or hydrogen bonding. The attractive interaction between neighboring molecules serves to stabilize the outer layer of the semiconductor nanocrystal. In the event that the linking moiety should dissociate from the semiconductor surface, the attractive interaction with its neighbors will help the molecule to remain closely associated with the semiconductor nanocrystal until its linking moiety is able to recoordinate to the surface.

Exemplary modifications include amide, ketone, ether and aromatic moieties, and the like, substituting in whole or in part for the hydrocarbon backbone or attached as pendant groups from the hydrocarbon backbone. The polar nature of the moieties promotes hydrogen bonding and other attractive interaction with neighboring molecules which stabilizes the coating and increases its robustness in aqueous solution.

Figure 3:
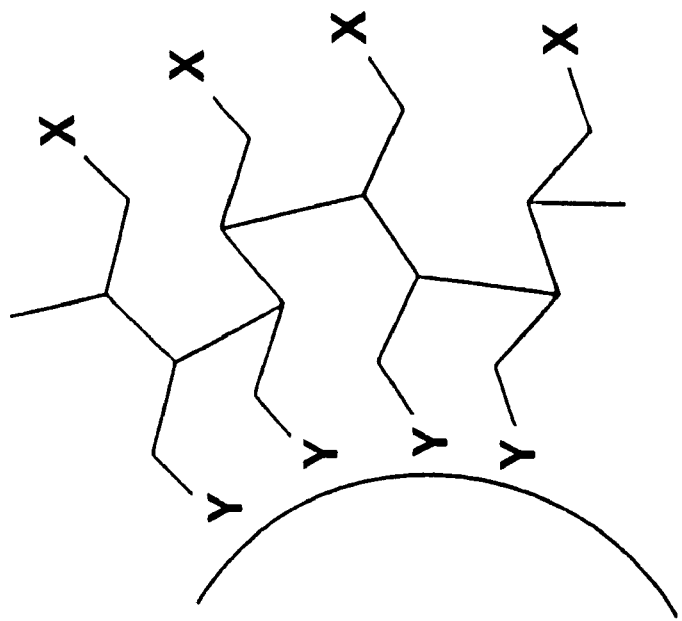
FIG. 3 is an illustration of a water-soluble nanocrystal of the invention having crosslinked hydrocarbon hydrophilic backbone.
Figure 3:
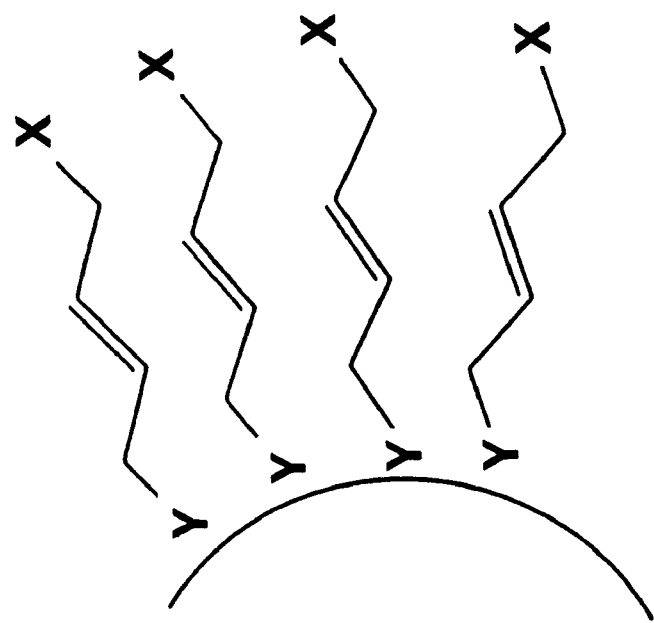

In other embodiments of the invention, the molecule of the outer layer is crosslinked to or polymerized with its neighboring molecules. Crosslinking provides stability to the layer by creating an effectively multidentate ligand across the semiconductor surface and significantly reducing ligand volatility and increasing the robustness and stability of the coating. Exemplary crosslinked networks are illustrated schematically in FIG. 3.

To this end, the hydrocarbon chain can include some degree of unsaturation, which can be crosslinked upon exposure to UV energy or other free radical initiator to bridge neighboring ligands. Hydrocarbon unsaturation (and subsequent crosslinks) retain the hydrophobicity desired to prevent the photoinduced degradation of the semiconductor surface.

Figure 4:
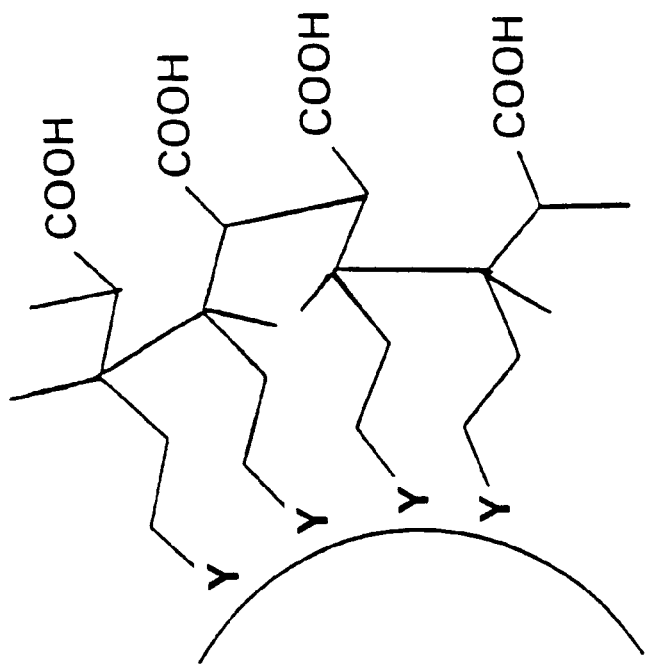
FIG. 4 is an illustration of a water-soluble nanocrystal of the invention comprising a polymethacrylate region.
Figure 4:
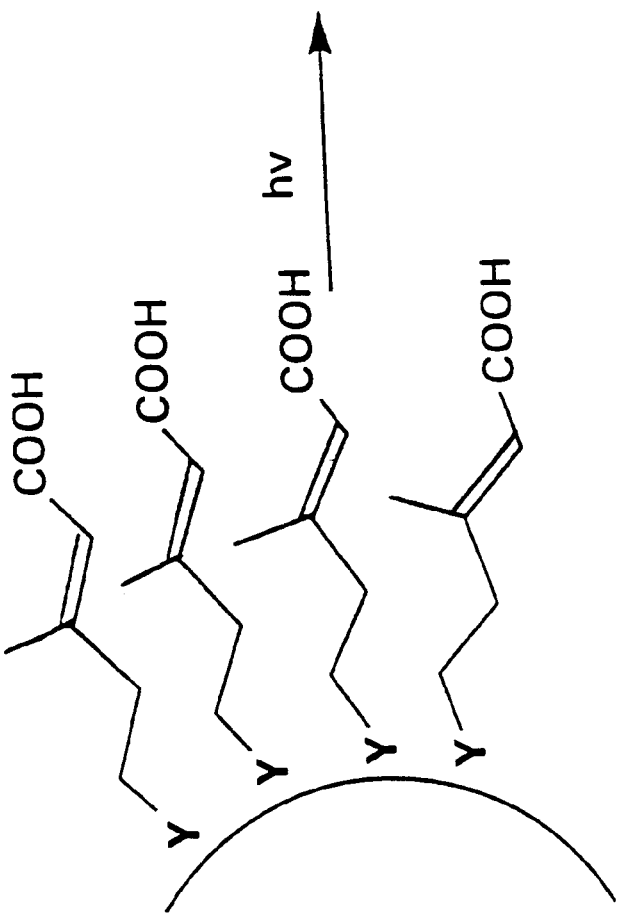

In one embodiment of the invention, the outer layer terminates in an unsaturated hydrophilic moiety that is capable of crosslinking or polymerizing. For example, the unsaturated moiety can be acrylic or methacrylate, which can be polymerized by exposure to free radical initiation, heat, UV energy, etc. to form poly(methacrylate), as is shown in FIG. 4. The result is a polymer network, in this example, poly(methacrylate), that interacts with and effectively shields the semiconductor nanocrystal from an aqueous environment. The poly(methacrylate) can be deprotonated to provide a charged surface to render the nanocrystal water-soluble. Other exemplary unsaturated moieties for polymerization include acrylic acid and polystyrene derivatized to include a water-solubilizing functional group, e.g., carboxylate and sulfonate, and the like.

In another embodiment of the invention, the outer layer is comprised of a block copolymer that provides the requisite, linking, hydrophilic and hydrophobic functionalities. The copolymer includes at least a first block which contains a pendant group capable of functioning as a linking moiety and a second block having a pendant group capable of functioning as a hydrophilic moiety. The polymer backbone can function as the hydrophobic region. The linking and hydrophilic moieties can be directly attached to the hydrocarbon backbone or they can be attached through intermediary spacing groups. For example, the linking group Y can terminate from an aromatic or alkyl spacing group to provides greater access to the semiconductor surface.

In one embodiment of the invention, the molecule has structural formula (V):

wherein $R^1$, $R^2$, $R^4$, $X^2$, $Y^2$, m' and n' are as defined above. In one exemplary embodiment of a molecule having structural formula (V), the molecule is a block copolymer having the formula,

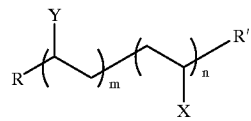

wherein X and Y are linking moieties and hydrophilic moieties, respectively, and can be any of the moieties discussed hereinabove. R and R' can be hydrogen, R can be a polar moiety and R' can be a non-polar moiety. The block copolymer can have a molecular weight of 300–50,000. The block sizes for the hydrophilic and linking moieties are preferably in the range of about 3 to 100.

Exemplary molecules for use in the invention have structural formula (I)

$$H_zX((CH_2)_nCO_2H)_y \qquad (I)$$

wherein X, z, n and y are as defined above, structural formula (II)

or structural formula (III)

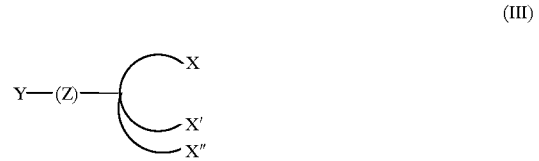

wherein Y, Z, X, X' and X" are as defined above, or structural formula (IV)

$$(R^1)_a-R^2-[(R^3)_b(R^4)_c]_d \qquad (IV)$$

wherein $R^1$, $R^2$, $R^3$, $R^4$, a, b, c, and d are as defined above.

Exemplary molecules for use in the outer layer of the water-soluble nanocrystal of the invention having the formula provided herein include long chain aminocarboxylic acids, $NH_2(CH_2)_nCOOH$, and phosphinocarboxylic acids, $P((CH_2)_nCOOH)_3$, and their oxides $O=P((CH_2)_nCOOH)_3$, wherein n is greater than or equal to 6, preferably n is greater than or equal to 8 and more preferably n is 10–12. The carboxylic acid can be deprotonated to provide the hydrophilic moiety. Other suitable molecules include bidentate ligands, such as, dihydrolipoic acid, $HSCH_2CH_2CH(SH)(CH_2)_4COOH$, or more generally, $HSCH_2CH_2CH(SH)(CH_2)_nCOOH$, where n is 1–10. The length of the ligand can be increased by standard carbodiimide coupling methods, producing a species with the formula $HSCH_2CH_2CH(SH)(CH_2)_4CONH(CH_2)_nCOOH$. The commercial availability of numerous precursors allows n to be easily varied from 2 to at least 10. Further detail of the carbodiimide coupling reaction can be found in Rich et al. (1979) *The Peptides* Vol. 1, Academic Press, pp. 241–2561.

Other suitable bidentate ligands include: the primary amine-containing analogues of the above molecule, $H_2NCH_2CH_2CH(NH_2)(CH_2)_nCOOH$; derivatives of ethylene diamine, such as $(HOOC(CH2)_n)HNCH_2CH_2NH((CH_2)_nCOOH)$; diphosphines such as $(HOOC(CH_2)_n)PCH_2CH_2P((CH_2)_nCOOH)_2$; and the corresponding diphosphine oxides $(HOOC(CH_2)_n)_2P(O)CH_2CH_2P(O)((CH_2)_nCOOH)_2$. An advantage to the use of the above-mentioned carboxylic acid derivatives it that they lend themselves to a wide range of chemistries. For example, the water-soluble semiconductor nanocrystal can be coupled with molecules having biological affinity for use in assaying. In another example, the water-soluble semiconductor nanocrystal can be coupled to beads, solid supports or objects of interest in order to track or identify an article. See co-pending applications Ser. No. 09/156,457 and 09/160,458, supra, for further details.

It will be readily apparent to one of ordinary skill in the art that the carboxylic acid moiety of the above-listed molecules can be substituted for a wide variety of charged or polar groups, including but not limited to, hydroxides, polyethers, such as polyethylene glycol and the like, and amines, as well as charged groups, such as carboxylates, sulfonates, phosphates, nitrates, ammonium salts and the like. Molecules such as listed herein above are commercially available or can be synthesized from methods and procedures well known in the art. It will be further apparent that the modifications described above with respect to hydrophobic regions and the hydrophilic groups can be incorporated into the molecule described immediately above in preparation of ligands suitable for use in the outer coating of the invention.

Figure 5A:
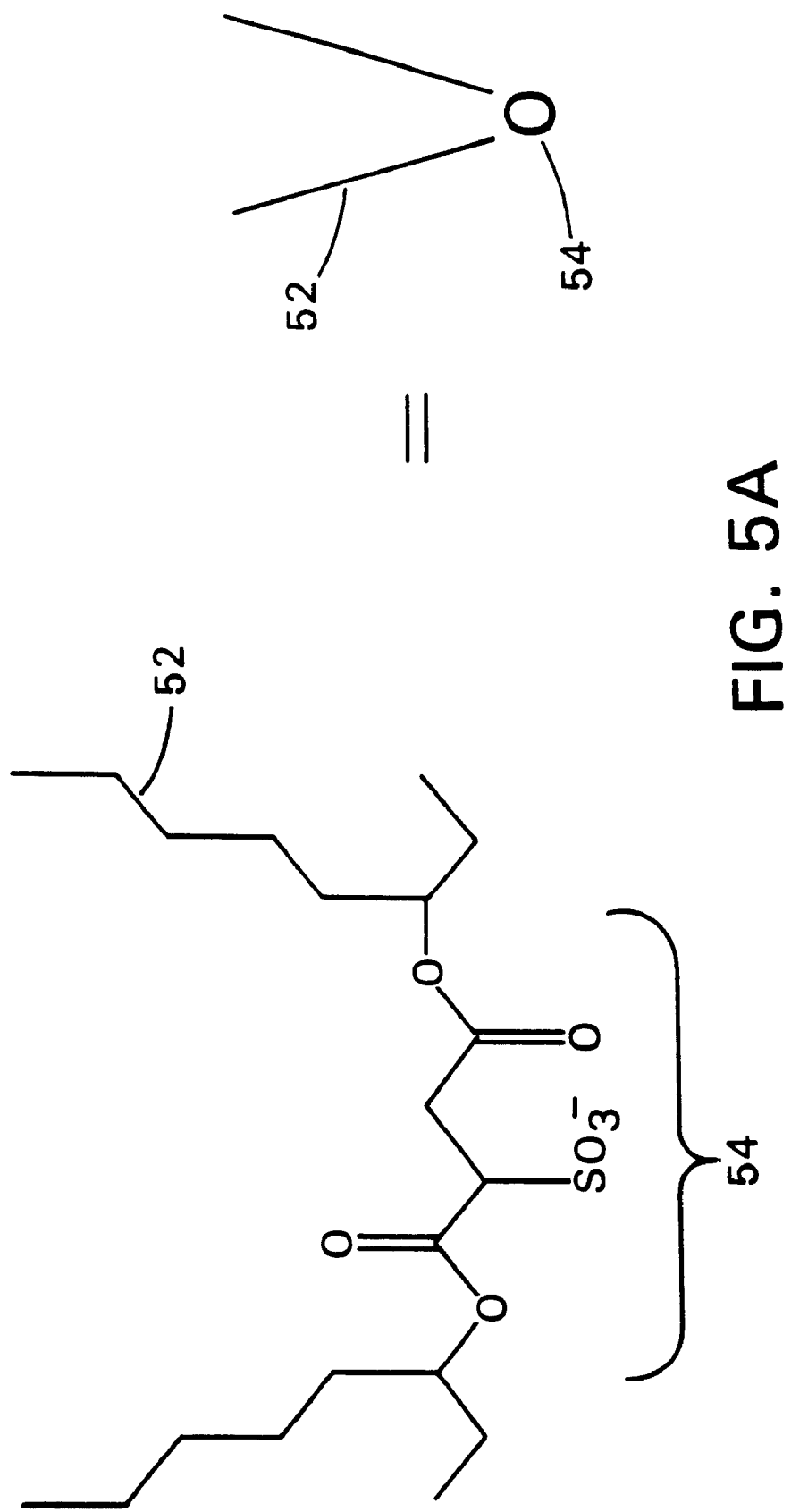
FIGS. 5A and 5B are schematic illustrations of a bilayer water-soluble nanocrystal of the invention.
Figure 5B:
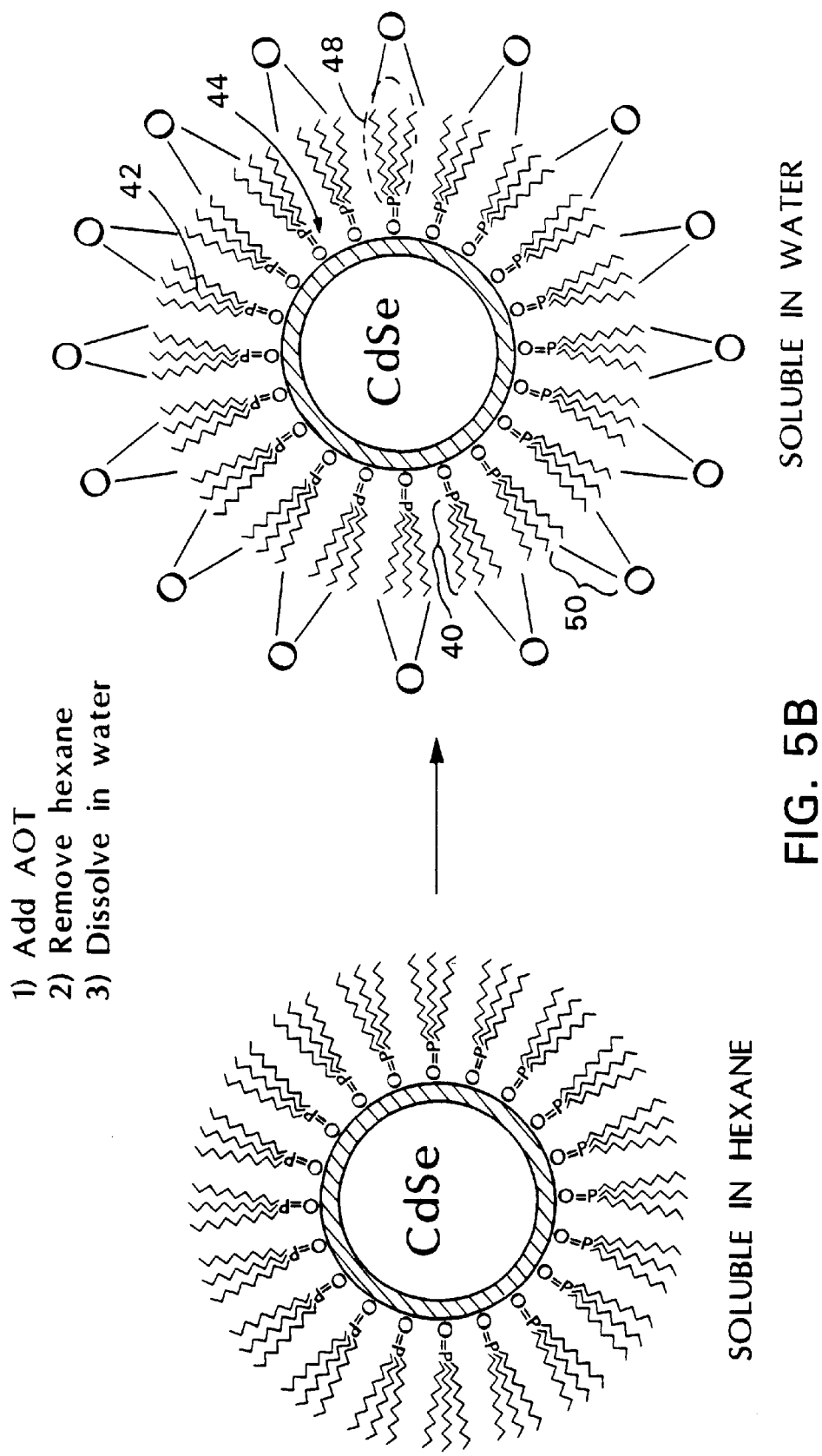

In another aspect of the invention, the water-soluble outer layer can be a bilayer comprising an inner layer having an affinity for the semiconductor surface and an outer layer terminating in a hydrophilic layer having an affinity for an aqueous medium. FIG. 5A illustrates an exemplary molecule used in the outer bilayer of the invention. The molecule, dioctyl sulfosuccinate (aerosol OT™), contains hydrophobic hydrocarbon regions 52 (denoted schematically as "- - - " in FIG. 5A) and a charged hydrophilic region 54 (denoted by "O" in FIG. 5A). An exemplary bilayer molecule is shown in FIG. 5B in which an inner layer 40 includes a molecule 42 (here TOPO) having a linking moiety 44 with an affinity for the semiconductor surface. A hydrophobic tail 48 extends from the linking moiety. The second outer layer 50 is comprised of a inner hydrophobic region 52 and an terminal hydrophilic moiety 54 for favorable interaction with an aqueous medium. The hydrophobic regions 48, 52 of the inner and outer layers, respectively, interact preferentially in the aqueous medium, to form a micelle encapsulating the nanocrystal therein. FIG. 5B also illustrates the displacement reaction which occurs to form the bilayer of the invention.

The inner layer can include those coordinating solvents typically used in the manufacture of the semiconductor nanocrystal. Exemplary molecules include trialkyl phosphines and phosphine oxides, such as trioctylphosphine oxide (TOPO), trioctylphosphine (TOP), tributylphosphine (TBP), and the like. Hexadecylamine is a possible solvent, in particular, for solvating ZnSe.

The second outer layer can include any surfactant having a non-polar tail and a polar head. Non-limiting examples of surfactants include sodium dioctyl sulfosuccinate (known by the trade name AOT soap), $C_{12}H_{25}(OC_2H_2C_2H_2)_{23}OH$ (Brij 35®), $C_{18}H_{37}(OC_2H_2C_2H_2)_{10}OH$ (Brij 76®) and $C_{18}H_{37}(OC_2H_2C_2H_2)_{20}OH$ (Brij 98®). Even common hand soap, e.g. IVORY® soap (essentially a sodium salt of fatty acids), has been successfully used in the preparation of water-soluble nanocrystals of the invention.

A method for the preparation of the water-soluble nanocrystal follows. The method is described for a CdSe(ZnS), i.e., a CdSe core with a ZnS shell, semiconductor nanocrystal, but it is understood that the method can be applied in the preparation of semiconductor nanocrystals from the known semiconductor materials.

A population of nearly monodisperse nanocrystals first is prepared. The actual size of the nanocrystals will vary depending upon the material used. For CdSe, particles range in size from about 12 Å to about 150 Å diameter with a particle size distribution of about 5–10% rms in diameter. The monodisperse nanocrystals can be obtained using a high-temperature colloidal growth process, optionally followed by size-selective precipitation. If spectral emission linewidths are not as narrow as desired, size-selective precipitation can be used to obtain a population of semiconductor nanocrystals of narrower particle size distribution. The monodisperse particle population can emit energy in a spectral range of no greater than about 40 nm full width at half max (FWHM), or 25 nm FWHM. See, Murray et al. (1993), supra, the Murray thesis (1995), supra, and Kuno et al., supra.

The semiconductor nanocrystal core can then be coated with the appropriate semiconductor overcoating layer, i.e., the shell. The coated nanocrystal can be prepared by introducing the substantially monodisperse first semiconductor nanocrystal and a precursor capable of thermal conversion into a second semiconductor material into a coordinating solvent. The coordinating solvent is maintained at a temperature sufficient to convert the precursor into the second semiconductor material yet insufficient to alter substantially the monodispersity of the first semiconductor nanocrystal. Preferably, the second semiconductor material has a band gap greater than that of the first semiconductor nanocrystal. An overcoating shell of the second semiconductor material is formed on the first semiconductor nanocrystal. The monodispersity of the nanocrystal is monitored during conversion of the precursor and overcoating of the first semiconductor nanocrystal. The particle size distribution can be refined further by size-selective precipitation. Further details in the preparation of a coated semiconductor nanocrystal for use in the water-soluble nanocrystal of the invention can be found in U.S. Ser. No. 08/969,302, filed Nov. 13, 1997 and entitled "Highly Luminescent Color-Selective Materials", and Dabbousi et al., supra, which are incorporated in their entireties by reference.

The outer surface of the nanocrystal, as formed, includes an organic layer derived from the coordinating solvent used during the capping layer growth process. The nanocrystal surface can be modified to obtain the water-soluble nanocrystal of the invention by repeated exposure to an excess of a competing coordinating group. For example, a dispersion of the semiconductor nanocrystal can be treated with a coordinating organic molecule, such as those described herein, to produce nanocrystals which disperse readily in water, but which no longer disperse in aliphatics. Such a surface exchange process can be carried out using a variety of molecules that are capable of coordinating or bonding to the outer surface of the capped semiconductor nanocrystal, such as by way of example, phosphines, thiols, amines, phosphine oxides and amine oxides.

Figure 6:
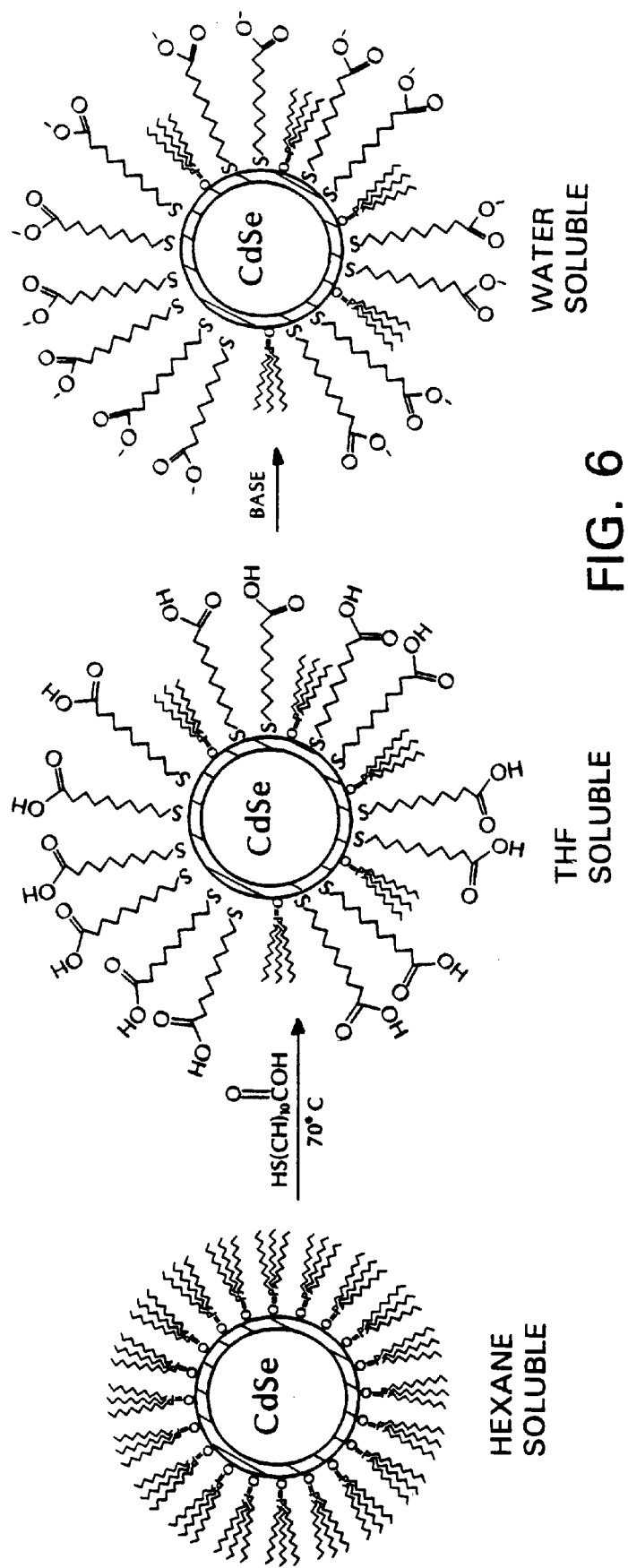
FIG. 6 is an illustration of the displacement reaction used in the formation of the water-soluble nanocrystal of the invention

A typical reaction is illustrated in FIG. 6. Semiconductor nanocrystals 60 are prepared in a coordinating organic solvent such as trioctylphosphine oxide (TOPO) which results in the formation of a passivating TOPO layer 62 on the surface of the semiconductor nanocrystal. This layer is displaced at least in part by the ligand 54, here represented as a long chain mercaptocarboxylic acid, comprising the outer layer of the invention in order to obtain water-soluble nanocrystal 66. Displacement can occur by dispersion of semiconductor nanocrystals or overcoated semiconductor nanocrystals in a medium containing high concentrations of the ligand used to form the outer coating. The medium can be a neat liquid comprising the ligand or it can be a highly concentrated solution. High concentrations drive the displacement reaction forward to maximize surface coverage of the nanocrystal by the molecule of the outer coating. Note that the displacement of the TOPO layer need not be complete in order to obtain a water-soluble nanocrystal.

Repeated exposure of the nanocrystal to the coordinating ligand solution may be desirable. The outer coating can be comprised of a mixture of the original polar organic solvent used in the preparation of the nanocrystal and the water-solubilizing molecule used in the outer coating of the invention. Substitution of the water-solubilizing molecule need only be sufficient to render the molecule water-soluble and need not be complete. In some embodiments, substitution is about 25–50% complete, preferably greater than 60% complete. The actual degree of substitution needed for solubility in water will depend on the number of charged or polar groups on the water-solubilizing molecule. Higher number of charged or polar groups can require a lower level of surface substitution in order to achieve water solubility.

It is also within the scope of the present invention to include other coordinating ligands on the outer coating of the nanocrystal. The additional ligands can be included to make available additional chemical reactions to the nanocrystal. For example coordinating ligands that terminate in reactive groups such as carboxylic acid, acyl halides and the like can be added to the outer surface of nanocrystal.

It is to be understood that while the invention has been described in conjunction with the preferred specific embodiments thereof, that the foregoing description as well as the examples which follow are intended to illustrate and not limit the scope of the invention. Other aspects, advantages and modifications within the scope of the invention will be apparent to those skilled in the art to which the invention pertains.

The following examples are intended to provide those of ordinary skill in the art with a complete disclosure and description of how to make and use the novel compositions of the invention, and are not intended to limit the scope of what the inventors regard as their invention in any way. Efforts have been made to ensure accuracy with respect to numbers used (e.g., amounts, temperatures, etc), but some experimental error and deviation should, of course, be allowed for. Unless indicated otherwise, parts are parts by weight, temperatures are in degrees centigrade, and pressure is at or near atmospheric.

The practice of the present invention will employ, unless otherwise indicated, conventional techniques of synthetic organic chemistry, biochemistry, molecular biology, and the like, which are within the skill of the art. Such techniques are explained fully in the literature. See, e.g., Kirk-Othmer's *Encyclopedia of Chemical Technology;* House's *Modern Synthetic Reactions;* the Marvel et al. text ORGANIC SYNTHESIS; Collective Volume 1, and the like.

EXAMPLE 1

Preparation of TOPO-capped CdSe(ZnS)

(a) Preparation of CdSe. Trioctylphosphine oxide (TOPO, 90% pure) and trioctylphosphine (TOP, 95% pure) were obtained from Strem and Fluka, respectively. Dimethyl cadmium ($CdMe_2$) and diethyl zinc ($ZnEt_2$) were purchased from Alfa and Fluka, respectively, and both materials were filtered separately through a 0.2 m filter in an inert atmosphere box. Trioctylphosphine selenide was prepare by dissolving 0.1 mols of Se shot in 100 ml of TOP thus producing a 1M solution of TOPSe. Hexamethyl (disilathiane) ($TMS_2S$) was used as purchased from Aldrich. HPLC grade n-hexane, methanol, pyridine and n-butanol were purchased from EM Sciences.

The typical preparation of TOP/TOPO-capped CdSe nanocrystals follows. TOPO (30 g) was placed in a flask and dried under vacuum (~1 Torr) at 180° C. for 1 hour. The flask was then filled with nitrogen and heated to 350° C. In an inert atmosphere drybox the following injection solution was prepared: $CdMe_2$ (200 microliters, 2.78 mmol), 1M TOPSe solution (4.0 mL, 4.0 mmol), and TOP (16 mL). The injection solution was thoroughly mixed, loaded into a syringe, and removed from the drybox.

The heat was removed from the reaction flask and the reagent mixture was delivered into the vigorously stirring TOPO with a single continuous injection. This produces a deep yellow/orange solution with a sharp absorption feature at 470–500 nm and a sudden temperature decrease to ~240° C. Heating was restored to the reaction flask and the temperature was gradually raised to 260–280° C.

Aliquots of the reaction solution were removed at regular intervals (5–10 min) and absorption spectra taken to monitor the growth of the crystallites. The best samples were prepared over a period of a few hours steady growth by modulating the growth temperature in response to changes in the size distribution, as estimated from the sharpness of the features in the absorption spectra. The temperature was lowered 5–10° C. in response to an increase in the size distribution. Alternatively, the reaction can also be stopped at this point. When growth appears to stop, the temperature is raised 5–10° C. When the desired absorption characteristics were observed, the reaction flask was allowed to cool to about 60° C. and 20 mL of butanol were added to prevent solidification of the TOPO. Addition of a large excess of methanol causes the particles to flocculate. The flocculate was separated from the supernatant liquid by centrifugation; the resulting powder can be dispersed in a variety of organic solvents (alkanes, ethers, chloroform, tetrahydrofuran, toluene, etc.) to produce an optically clear solution.

The powder can be further optimized in an optional size selective precipitation procedure. Nanocrystallites were dispersed in a solution of ~10% butanol in hexane. Methanol was then added dropwise to this stirring solution until opalescence persisted. Separation of supernatant and flocculate by centrifugation produced a precipitate enriched with the largest crystallites in the sample. This procedure was repeated until no further sharpening of the optical absorption spectrum was noted. Size-selective precipitation can be carried out in a variety of solvent/nonsolvent pairs, including pyridine/hexane and chloroform/methanol.

(b) Preparation of CdSe(ZnS). A flask containing 5 g of TOPO was heated to 190 C under vacuum for several hours then cooled to 60° C. after which 0.5 mL trioctylphosphine (TOP) was added. Roughly 0.1–0.4 micromols of CdSe nanocrystals dispersed in hexane were transferred into the reaction vessel via syringe and the solvent was pumped off.

Diethyl zinc ($ZnEt_2$) and hexamethyldisilathiane (($TMS)_2S$) were used as the Zn and S precursors, respectively. Particle size distribution for a particular sample was determined by comparison of the optical data to those of known semiconductor nanocrystals of known particle size. The amounts of Zn and S precursors needed to grow a ZnS shell of desired thickness for each CdSe sample was calculated based on the ratio of the shell volume to that of the core assuming a spherical core and shell and taking into account the bulk lattice parameters of CdSe and ZnS. For larger particles, the ratio of Zn to Cd necessary to achieve the same thickness shell is less than for the smaller nanocrystals. The actual amount of ZnS that grows onto the CdSe cores was generally less than the amount added due to incomplete reaction of the precursors and to loss of some material on the walls of the flask during the addition.

Equimolar amounts of the precursors were dissolved in 2–4 mL TOP inside an inert atmosphere glove box. The precursor solution was loaded into a syringe and transferred to an addition funnel attached to the reaction flask. The reaction flask containing CdSe nanocrystals dispersed in TOPO and TOP was heated under an atmosphere of $N_2$. The temperature at which the precursors were added ranged from 140° C. for 23 Å diameter nanocrystals to 220° C. for 55 Å diameter nanocrystals. When the desired temperature was reached the Zn and S precursors were added dropwise to the vigorously stirring reaction mixture over a period of 5–10 minutes.

After the addition was complete the mixture was cooled to 90° C. and left stirring for several hours. Butanol (5 mL) was added to the mixture to prevent the TOPO from solidifying upon cooling to room temperature. The overcoated particles were stored in their growth solution to ensure that the surface of the nanocrystals remained passivated with TOPO. They were later recovered in powder form by precipitating with methanol and redispersing into a variety of solvents including hexane, chloroform, toluene, THF and pyridine.

EXAMPLE 2

Preparation of a Water-soluble Semiconductor Nanocrystals Using Long Chain Mercaptocarboxylic Acid.

TOPO-capped CdSe(ZnS) semiconductor nanocrystals were prepared as described in Example 1. The overcoated CdSe(ZnS) nanocrystals were precipitated from the growth solution using a mixture of butanol and methanol. To obtain the precipitated semiconductor nanocrystals, the solution was centrifuged for 5–10 min,, the supernatant was decanted and the residue was washed with methanol (2x).

The residue was weighed. The weight of the TOPO cap was assumed to be 30% of the total weight; and a 30-fold molar excess of the new capping molecule, 11-mercaptoundecanoic acid (MUA) was added. The residue and MUA (neat solution) were stirred at 60° C. for 8–12 hours. A volume of tetrahydrofuran (THF) equal to the added MUA was added to the MUA/nanocrystal mixture, while the mixture was still hot. A clear solution resulted and the coated semiconductor nanocrystals were stored under THF.

The coated semiconductor nanocrystals are rendered water-soluble by deprotonation of the carboxylic acid functional group of the MUA. The deprotonation was accomplished by adding a suspension of potassium t-butoxide in THF to the MUA-semiconductor nanocrystal/THF solution. A gel resulted, which was then centrifuged and the supernatant liquid was poured off. The residue was washed twice with THF, centrifuged each time and the supernatant liquid poured off. The final residue was allowed to dry in air for 10 minutes. Deionized water (Millipore) was added to the residue until a clear solution formed.

The resultant coated semiconductor nanocrystals were tested for photoluminescent quantum yield. A CdSe semiconductor nanocrystal with a four-monolayer coating of ZnS coated as described had an absorption band a 480 nm and a photoluminescent band at 500 nm, with a quantum yield of 12%. A second CdSe semiconductor nanocrystal with a four monolayer coating of ZnS coated as described had an absorption band a 526 nm and a photoluminescent band at 542 nm, with a quantum yield of 18%.

EXAMPLE 3

Preparation of a Water-soluble Semiconductor Nanocrystal Using a Multidentate Ligand.

A water-soluble semiconductor nanocrystal was prepared as described in Example 2, except that the bidentate ligand, dihydrolipoic acid was used.

The synthesis of a bidentate dithiol ligand was accomplished via the reduction of the coenzyme lipoic acid. The general procedure was described in Gunsalus et al. (1956) *J. Am. Chem. Soc.* 78:1763–1766. Sodium borohydride (1.2 g) was added in 30–50 mg portions to a stirring suspension of lipoic acid (6.0 g) in 117 mL of 0.25 M sodium bicarbonate in 0° C. water. The reaction was stirred for 45 minutes at 0° C., after which 100 mL toluene was added and the mixture was acidified to pH ~2 with hydrochloric acid. The toluene layer was collected and saved. The aqueous layer was washed three times with 15 mL toluene. The organic layers were combined, dried with anhydrous magnesium sulfate, filtered, and the solvent removed under vacuum, leaving behind the product dihydrolipoic acid as a yellow oil (yield 80%).

Cap exchange was performed using the same procedure as described for 11-mercaptoundecanoic acid. TOPO-capped CdSe(ZnS) semiconductor nanocrystals were precipitated from solution and washed twice with methanol. The remaining powder was dissolved (under nitrogen) at 70° C. in the minimum amount (usually 300–600 mg) of dihydrolipoic acid necessary to produce a clear solution. This mixture was stirred at 70° C. for 6 hours, then stored at room temperature. The nanocrystals were rendered water soluble by treatment with potassium t-butoxide in THF, as described for the mercaptocarboxylic acid ligands.

EXAMPLE 4

Preparation of a Water-soluble Semiconductor Nanocrystal Using a Surfactant.

TOPO-capped CdSe(ZnS) semiconductor nanocrystals were prepared as described in Example 1. The semiconductor nanocrystals were dissolved in hexane to give a solution that was approximately 0.001–0.01 molar concentration of CdSe(ZnS) nanocrystals. Sufficient surfactant sodium dioctylsulfosuccinate (trade name AOT) was added to the mixture to produce a solution that is 5% surfactant by weight (but liquid IVORY® soap (essentially a sodium salt of fatty acids) also worked). The hexane solvent was evaporated under vacuum. The resulting solid residue dissolved in water to give a clear solution whose quantum yield was approximately the same as the initial sample (~75% of the original value).

What is claimed is:

1. A water-soluble semiconductor nanocrystal capable of energy emission, comprising:
a semiconductor nanocrystal core having a selected band gap energy;
a shell layer overcoating the semiconductor nanocrystal core, the shell comprised of a semiconductor material having a band gap energy greater than that of the core;
an outer layer comprising a molecule having a first portion comprising at least two linking groups for attachment to the nanocrystal and a second portion comprising at least one hydrophilic group.

2. A water-soluble semiconductor nanocrystal capable of energy emission, comprising:
a semiconductor nanocrystal core having a selected band gap energy; and an outer layer comprising a molecule having a first portion comprising at least one linking group for attachment to the nanocrystal and a second portion comprising at least one hydrophilic group, the molecule being selected from the group consisting of:
a structure of formula (I),

$$H_zX((CH_2)_nCO_2H)_y \quad (I)$$

or a salt thereof, wherein: X is the first portion of the ligand and is N, P or O=P;
n is greater than or equal to 6; and z and y are selected to satisfy the valence requirements of X;
a structure of formula (II),

(II)

wherein: Y is the hydrophilic moiety; Z is a hydrophobic region having a backbone of at least six atoms; X and X' are individually or together the linking groups, are the same or different and are selected from the group of S, N, P and O=P, each of X and X' optionally including other substituents in order to satisfy valence requirements, and atoms bridging X and X' are selected to form a 5-membered to 8-membered ring upon coordination to the nanocrystal surface;
a structure of formula (III),

(III)

wherein: Y is the hydrophilic moiety; Z is a hydrophobic region having a backbone of at least six atoms; X, X' and X" are individually or together linking groups, are the same or different and are selected from the group of S, N, P and O=P, each of X, X' and X" optionally including other substituents in order to satisfy valence requirements; atoms bridging X and X' are selected to form a 5-membered to 8-membered ring upon coordination to the semiconductor surface, atoms bridging X and X" are selected to form a 5-membered to 8-membered ring upon coordination to the semiconductor surface, and atoms bridging X' and X" are selected to form a 5-membered to 8-membered ring upon coordination to the semiconductor surface;
a structure of formula (IV),

$$(R^1)_a-R^2-[(R^3)_b(R^4)_c]_d \quad (IV)$$

wherein:
$R^1$ is the first portion and is selected from the group consisting of heteroalkyl, heteroalkenyl, heteroalkynyl, —OR, —SR, —NHR, —NR'R", —N(O)HR, —N(O)R'R", —PHR, PR'R", —P(NR'R")NR'R", —P(O)R'R", —P(O)(NR'R")NR'R", —P(O)(OR')OR", —P(O)OR, P(O)NR'R", —P(S)(OR')OR", and —P(S)OR wherein R, R' and R" are independently selected from the group consisting of H, a branched or unbranched alkyl, a branched or unbranched alkenyl, a branched or unbranched alkynyl, a branched or unbranched heteroalkyl, a branched or unbranched heteroalkenyl and a branched or unbranched heteroalkynyl, with the proviso that when a is greater than 1 the R' groups are the same or different or are linked to form a six-, seven-, eight-, nine- or ten-membered cycloalkyl, cycloalkenyl, heterocyclic, aryl, heteroaryl, or a six-to thirty-membered crown ether or heterocrown ether;
$R^2$ is selected from a bond, a branched or unbranched alkylene, a branched or unbranched alkenylene, a branched or unbranched heteroalkylene, a branched or unbranched heteroalkenylene, cycloalkyl, cycloalkenyl, cycloalkynyl, heterocyclic, aryl and heteroaryl;
$R^3$ is selected from a branched or unbranched alkylene, a branched or unbranched alkenylene, a branched or unbranched heteroalkylene, a branched or unbranched heteroalkenylene, cycloalkyl, cycloalkenyl, cycloalkynyl, heterocyclic, aryl and heteroaryl;
$R^4$ is the second portion and is selected from the group consisting of hydrogen, a carboxylate, a thiocarboxylate, an amide, an imide, a hydrazine, a sulfonate, a sulfoxide, a sulfone, a sulfite, a phosphate, a phosphonate, a phosphonium, an alcohol, a thiol, an amine, an ammonium, an alkyl ammonium, a nitrate, a sugar moiety, and a five-, six-, seven-, eight-, nine- or ten-membered cycloalkyl, cycloalkenyl, cycloalkynyl, heterocyclic, aryl, or heteroaryl;
a is 1, 2, 3 or 4;
b is 0, 1, 2 or 3;
c is 1, 2 or 3; and
d is 2 or 3, wherein the $R^3$ groups are the same or different or are linked together to form a five-, six-, seven-, eight-, nine- or ten-membered cycloalkyl, cycloalkenyl, heterocyclic, aryl, or heteroaryl;
a structure of formula (V),

(V)

wherein:
$X^2$ and $Y^2$ are the same or different and are mer units selected from the group consisting of acrylate, styrene, imide, acrylamide, ethylene, vinyl, diacetylene, phenylene-vinylene, amino acid, sugar, sulfone, pyrrole, imidazole, thiophene and ether;
$R^1$ is the first portion and is selected from the group consisting of heteroalkyl, heteroalkenyl, heteroalkynyl, —OR —SR —NHR, —NR'R", —N(O)HR, —N(O)R'R", —PHR, —PR'R", —P(NR'R")NR'R",—P(O)R'R", —P(O)(NR'R")NR'R", —P(O)(OR')OR", —P(O)OR —P(O)NR'R", —P(S)(OR')OR", and —P(S)OR, wherein R, R' and R" are independently selected from the group consisting of H, a branched or unbranched alkyl, a branched or unbranched alkenyl, a branched or unbranched alkynyl, a branched or unbranched heteroalkyl, a branched or unbranched heteroalkenyl and a branched or unbranched heteroalkynyl, with the proviso that when a is greater than 1 the $R^1$ groups can be the same or different or can be linked to form a six-, seven-, eight-, nine- or ten-membered cycloalkyl, cycloalkenyl, heterocyclic, aryl, heteroaryl, or a six- to thirty-membered crown ether or heterocrown ether;

$R^2$ is selected from a bond, a branched or unbranched alkylene, a branched or unbranched alkenylene, a branched or unbranched heteroalkylene, a branched or unbranched heteroalkenylene, cycloalkyl, cycloalkenyl, cycloalkynyl, heterocyclic, aryl and heteroaryl;

$R^4$ is the second portion and is selected from the group consisting of hydrogen, a carboxylate, a thiocarboxylate, an amide, an imide, a hydrazine, a sulfonate, a sulfoxide, a sulfone, a sulfite, a phosphate, a phosphonate, a phosphonium, an alcohol, a thiol, an amine, an ammonium, an alkyl ammonium, a nitrate, a sugar moiety, and a five-, six-, seven-, eight-, nine- or ten-membered cycloalkyl, cycloalkenyl, cycloalkynyl, heterocyclic, aryl, or heteroaryl;

m' is in the range of about 3 to 100; and n' is in the range of about 3 to 100; and a structure having formula,

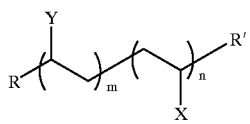

wherein: the Xs are the same or different and are selected from the group consisting of S, N, P and O=P, and optionally include other substituents to satisfy valence requirements; the Ys are a hydrophilic moiety; R is H or a polar moiety; R' is H or a non-polar moiety; m is in the range about 3 to 100; and n is in the range about 3 to 100.

3. The water-soluble nanocrystal of claim 1 or 2, wherein the molecule has structural formula (I), $$H_zX((CH_2)_nCO_2H)_y \qquad (I)$$

or a salt thereof, wherein:

X is the first portion of the ligand and is N, P or O=P;

n is greater than or equal to 6; and z and y are selected to satisfy the valence requirements of X.

4. The water-soluble nanocrystal of claim 1 or 2, wherein the molecule has structural formula (II), (II)

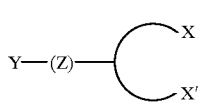

wherein:

Y is the hydrophilic moiety;

Z is a hydrophobic region having a backbone of at least six atoms;

X and X' are individually or together the linking groups, are the same or different and are selected from the group of S, N, P and O=P, each of X and X' optionally including other substituents in order to satisfy valence requirements and atoms bridging X and X' are selected to form a 5-membered to 8-membered ring upon coordination to the nanocrystal surface.

5. The water-soluble nanocrystal of claim 1 or 2, wherein the molecule has structural formula (III), (III)

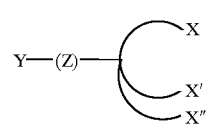

wherein:

Y is the hydrophilic moiety;

Z is a hydrophobic region having a backbone of at least six atoms;

X, X' and X" are individually or together linking groups, are the same or different and are selected from the group of S, N, P and O=P, each of X, X' and X" optionally including other substituents in order to satisfy valence requirements, and atoms bridging X and X' are selected to form a 5-membered to 8-membered ring upon coordination to the semiconductor surface, atoms bridging X and X" are selected to form a 5-membered to 8-membered ring upon coordination to the semiconductor surface, and atoms bridging X' and X" are selected to form a 5-membered to 8-membered ring upon coordination to the nanocrystal surface.

6. The water-soluble nanocrystal of claim 1 or 2, wherein the molecule has the structural formula (IV), $$(R^1)_a—R^2—[(R^3)_b(R^4)_c]_d \qquad (IV)$$

wherein:

$R^1$ is the first portion and is selected from the group consisting of heteroalkyl, heteroalkenyl, heteroalkynyl, —OR, —SR, —NHR, —NR'R", —N(O)HR, —N(O)R'R", —PHR, —PR'R", —P(NR'R")NR'R", —P(O)R'R", —P(O)(NR'R")NR'R", —P(O)(OR')OR", —P(O)OR, —P(O)NR'R", —P(S)(OR')OR", and —P(S)OR wherein R, R'and R" are independently selected from the group consisting of H, a branched or unbranched alkyl, a branched or unbranched alkenyl, a branched or unbranched alkynyl, a branched or unbranched heteroalkyl, a branched or unbranched heteroalkenyl and a branched or unbranched heteroalkynyl, with the proviso that when a is greater than 1 the $R^1$ groups are the same or different or are linked to form a six-, seven-, eight-, nine- or ten-membered cycloalkyl, cycloalkenyl, heterocyclic, aryl, heteroaryl, or a six- to thirty-membered crown ether or heterocrown ether;

$R^2$ is selected from a bond, a branched or unbranched alkylene, a branched or unbranched alkenylene, a branched or unnbranched alkylene, a branched or unbranched heteroalkenylene, cycloalkyl, cycloalkenyl, cycloalkynyl, heterocyclic, aryl and heteroaryl;

$R^3$ is selected from a branched or unbranched alkylene, a branched or unbranched alkenylene, a branched or unbranched heteroalkylene, a branched or unbranched heteroalkenylene, cycloalkyl, cycloalkenyl, cycloalkynyl, heterocyclic, aryl and heteroaryl;

R⁴ is the second portion and is selected from the group consisting of hydrogen, a carboxylate, a thiocarboxylate, an amide, an imide, a hydrazine, a sulfonate, a sulfoxide, a sulfone, a sulfite, a phosphate, a phosphonate, a phosphonium, an alcohol, a thiol, an amine, an ammonium, an alkyl ammonium, a nitrate, a sugar moiety, and a five-, six-, seven-, eight-, nine- or ten-membered cycloalkyl, cycloalkenyl, cycloalkynyl, heterocyclic, aryl, or heteroaryl;

a is 1, 2, 3 or 4;

b is 0, 1, 2 or 3;

c is 0, 1, 2 or 3; and d is 0, 1, 2 or 3, wherein when d is 2 or 3 the R³ groups are the same or different or are linked together to form a five-, six-, seven-, eight-, nine- or ten-membered cycloalkyl, cycloalkenyl, heterocyclic, aryl, or heteroaryl.

7. The water-soluble nanocrystal of claim 6, wherein R¹ is a thiol, a phosphine, a phosphine oxide, or an amine.

8. The water-soluble nanocrystal of claim 6, wherein R² contains between 6 and 20 atoms.

9. The water-soluble nanocrystal of claim 8, wherein R² is a linear alkylene, alkenylene, alkynylene, heteroalkylene, heteroalkenylene, heteroalkynylene, a cycloalkyl or a heterocyclic.

10. The water-soluble nanocrystal of claim 6, wherein b is 1, 2 or 3, and R³ contains between 6 and 20 atoms.

11. The water-soluble nanocrystal of claim 10, wherein R³ is a linear alkylene, alkenylene, alkynylene, heteroalkylene, heteroalkenylene, heteroalkynylene, a cycloalkyl or heterocyclic.

12. The water-soluble nanocrystal of claim 6, wherein R⁴ is a carboxylate, a phosphonate, a sulfonate or an ammonium.

13. The water-soluble nanocrystal of claim 6, wherein the molecule is a multidentate ligand.

14. The water-soluble nanocrystal of claim 1 or 2, wherein the molecule comprises structural formula (V),

  (V)

wherein:

X² and Y² are the same or different and are mer units selected from the group consisting of acrylate, styrene, imide, acrylamide, ethylene, vinyl, diacetylene, phenylene-vinylene, amino acid, sugar, sulfone, pyrrole, imidazole, thiophene and ether;

R¹ is the first portion and is selected from the group consisting of heteroalkyl, heteroalkenyl, heteroalkynyl, —OR —SR —NHR, —NR'R", —N(O)HR, —N(O)R'R", —PHR, —PR'R", —P(NR'R")NR'R",—P(O)R'R", —P(O)(NR'R")NR'R", —P(O)(OR')OR", —P(O)OR —P(O)NR'R", —P(S)(OR')OR", and —P(S)OR, wherein R, R' and R" are independently selected from the group consisting of H, a branched or unbranched alkyl, a branched or unbranched alkenyl, a branched or unbranched alkynyl, a branched or unbranched heteroalkyl, a branched or unbranched heteroalkenyl and a branched or unbranched heteroalkynyl, or is linked to form a six-, seven-, eight-, nine- or ten-membered cycloalkyl, cycloalkenyl, heterocyclic, aryl, heteroaryl, or a six- to thirty-membered crown ether or heterocrown ether;

R² is selected from a bond, a branched or unbranched alkylene, a branched or unbranched alkenylene, a branched or unbranched heteroalkylene, a branched or unbranched heteroalkenylene, cycloalkyl, cycloalkenyl, cycloalkynyl, heterocyclic, aryl and heteroaryl;

R⁴ is the second portion and is selected from the group consisting of hydrogen, a carboxylate, a thiocarboxylate, an amide, an imide, a hydrazine, a sulfonate, a sulfoxide, a sulfone, a sulfite, a phosphate, a phosphonate, a phosphonium, an alcohol, a thiol, an amine, an ammonium, an alkyl ammonium, a nitrate, a sugar moiety, and a five-, six-, seven-, eight-, nine- or ten-membered cycloalkyl, cycloalkenyl, cycloalkynyl, heterocyclic, aryl, or heteroaryl;

m' is in the range of about 3 to 100; and n' is in the range of about 3 to 100.

15. The water-soluble nanocrystal of claim 1 or 2, wherein the molecule comprises the formula,

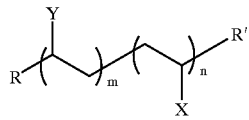

wherein:

the Xs are the same or different and are selected from the group consisting of S, N, P and O=P, and optionally include other substituents to satisfy valence requirements; the Ys are a hydrophilic moiety; R is H or a polar moiety; R' is H or a non-polar moiety; m is in the range about 3 to 100; and n is in the range about 3 to 100.

16. The water-soluble nanocrystal of claim 14, wherein the molecule is a multidentate ligand.

17. The water-soluble nanocrystal of claim 1 or 2, wherein the molecule is a multidentate ligand.

18. A water-soluble semiconductor nanocrystal capable of energy emission, comprising:

a semiconductor nanocrystal core having a selected band gap energy;

a shell layer overcoating the semiconductor nanocrystal core, the shell comprised of a semiconductor material having a band gap energy greater than that of the semiconductor nanocrystal; and a bilayer overcoating the shell, the bilayer comprising:

an inner layer having affinity for the shell; and an outer layer comprising a molecule having a hydrophilic group spaced apart from the inner layer by a hydrophobic region adjacent to the inner layer.

19. The water-soluble nanocrystal of claim 18, wherein the inner layer comprises a coordinating lyophilic compound.

20. The water-soluble nanocrystal of claim 19, wherein the coordinating lyophilic compound is selected from the group consisting of trialkyl phosphines, trialkyl phosphine oxides, and alkyl amines.

21. The water-soluble nanocrystal of claim 18, wherein the outer layer comprises a surfactant.

22. The water-soluble nanocrystal of claim 21, wherein the surfactant is selected from the group consisting of sodium dioctyl sulfosuccinate, $C_{12}H_{25}(OCH_2CH_2)_{23}OH$, $C_{18}H_{37}(OCH_2CH_2)_{10}OH$ and $C_{18}H_{37}(OC_2CH_2)_{20}OH$.

23. The water-soluble nanocrystal of claim 1, or 18, wherein the nanocrystal core is a Group II–VI, Group III–V or Group IV semiconductor.

24. The water-soluble nanocrystal of claim 23, wherein the core is a member of a monodisperse particle population.

25. The water-soluble nanocrystal of claim 24, wherein the monodisperse particle population is characterized in that when irradiated the population emits light in a spectral range less than about 40 nm full width at half maximum (FWHM).

26. The water-soluble nanocrystal of claim 25, wherein the monodisperse particle population is characterized in that when irradiated the population emits light in a spectral range less than about 25 nm full width at half maximum (FWHM).

27. The water-soluble nanocrystal of claim 24, wherein the monodisperse particle population is characterized in that it exhibits no more than about a 10% rms deviation in the diameter of the core.

28. The water-soluble nanocrystal of claim 27, wherein the monodisperse particle population is characterized in that it exhibits no more than about 5% rms deviation in the diameter of the core.

29. The water-soluble nanocrystal of claim 23, wherein the core comprises CdS, CdSe, CdTe, ZnS, ZnSe, ZnTe, MgTe, GaAs, GaP, GaSb, GaN, HgS, HgSe, HgTe, InAs, InP, InSb, InN, AlAs, AlP, AlSb, AlS, PbS, PbSe, Ge, Si, an alloy thereof, or a mixture thereof.

30. The water-soluble nanocrystal of claim 1 or 18, wherein the core comprises CdS, CdSe, CdTe, ZnS, ZnSe, ZnTe, MgTe, GaAs, Gap, GaSb, GaN, HgS, HgSe, HgTe, InAs, InP, InSb, InN, AlAs, AlP, AlSb, AlS, PbS, PbSe, Ge, Si, an alloy thereof, or a mixture thereof, and the shell comprises ZnO, ZnS, ZnSe, ZnTe, CdO, CdS, CdSe, CdTe, MgS, MgSe, GaAs, GaN, GaP, GaAs, GaSb, HgO, HgS, HgSe, HgTe, InAs, InN, InP, InSb, AlAs, AlN, AlP, AlSb, an alloy thereof, or a mixture thereof.

31. The water-soluble nanocrystal of claim 1 or 18, wherein the core is CdSe and the shell is ZnS.

* * * * *